US012741269B2

(12) United States Patent
Wortman et al.

(10) Patent No.: US 12,741,269 B2
(45) Date of Patent: Sep. 22, 2026

(54) DUAL-LAYER HOLLOW FIBER MEMBRANES AND METHODS OF MAKING AND USE

(71) Applicant: REGENTS OF THE UNIVERSITY OF MICHIGAN, Ann Arbor, MI (US)

(72) Inventors: James Wortman, Ann Arbor, MI (US); Suljo Linic, Ann Arbor, MI (US); Ali Hussain Motagamwala, Ann Arbor, MI (US)

(73) Assignee: REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 10 days.

(21) Appl. No.: 18/199,746

(22) Filed: May 19, 2023

(65) Prior Publication Data

US 2023/0372901 A1 Nov. 23, 2023

Related U.S. Application Data

(60) Provisional application No. 63/344,437, filed on May 20, 2022.

(51) Int. Cl.

*B01J 23/10* (2006.01)
*B01D 53/22* (2006.01)
*B01D 67/00* (2006.01)
*B01D 69/02* (2006.01)
*B01D 69/08* (2006.01)
*B01D 69/14* (2006.01)
*B01D 71/68* (2006.01)

(Continued)

(52) U.S. Cl.

CPC ............ *B01J 23/10* (2013.01); *B01D 53/228* (2013.01); *B01D 67/0016* (2013.01); *B01D 69/02* (2013.01); *B01D 69/085* (2013.01); *B01D 69/088* (2013.01); *B01D 69/145* (2013.01); *B01D 71/68* (2013.01); *B01J 35/40* (2024.01); *B01J 35/59* (2024.01); *B01J 37/0018* (2013.01); *B01J 37/088* (2013.01); *C07C 2/84* (2013.01); *B01D 2053/224* (2013.01); *B01D 2325/0233* (2022.08); *B01D 2325/04* (2013.01); *B01D 2325/10* (2013.01); *C07C 2523/10* (2013.01)

(58) Field of Classification Search

CPC ... B01J 23/10; B01J 35/59; B01J 35/40; B01J 37/0018; B01J 37/088; B01D 53/228; B01D 67/0016; B01D 69/02; B01D 69/085; B01D 69/088; B01D 69/145; B01D 71/68; C07C 2/84

See application file for complete search history.

(56) References Cited

U.S. PATENT DOCUMENTS 8,741,031 B2 6/2014 Kosuri et al.
8,771,404 B2 7/2014 Li et al.

(Continued)

OTHER PUBLICATIONS

Wortman et al., Optimizing hierarchical membrane/catalyst systems for oxidative coupling of methane using additive manufacturing and Supplementary Information, Nat. Mat., 22: 1523-1530 (2023).

(Continued)

*Primary Examiner* — Maria V Ewald
*Assistant Examiner* — Ethan Weydemeyer
(74) *Attorney, Agent, or Firm* — MARSHALL, GERSTEIN & BORUN LLP

(57) ABSTRACT

An asymmetric hollow fiber membrane for oxidative coupling of methane reactions.

25 Claims, 10 Drawing Sheets

(51) Int. Cl.

| | |
|---|---|
| ***B01J 35/02*** | (2006.01) |
| ***B01J 35/06*** | (2006.01) |
| ***B01J 35/40*** | (2024.01) |
| ***B01J 35/59*** | (2024.01) |
| ***B01J 37/00*** | (2006.01) |
| ***B01J 37/08*** | (2006.01) |
| ***C07C 2/84*** | (2006.01) |

(56) References Cited

U.S. PATENT DOCUMENTS

| | | | | |
|---|---|---|---|---|
| 11,148,100 | B2 | 10/2021 | Sohail et al. | |
| 2003/0140790 | A1 | 7/2003 | Herczeg | |
| 2010/0331595 | A1* | 12/2010 | Chinta | C07C 2/84 585/500 |
| 2013/0025458 | A1* | 1/2013 | Li | C04B 35/62897 264/171.12 |
| 2015/0053611 | A1 | 2/2015 | Wang et al. | |
| 2015/0096506 | A1* | 4/2015 | Kelly | B01J 19/243 122/32 |
| 2015/0298102 | A1* | 10/2015 | Kawi | B01J 23/44 502/4 |

OTHER PUBLICATIONS

Accardo, et al., Li/Gd Co-doped Barium-cerate Perovskites for LT-SOFCs, AIP Conf. Proc. 2196, 020032, (2019).

Ahmad, et al., Co-extruded Dual-layer Hollow Fiber for Micro-tubular SOFC, International Journal of Hydrogen Energy, 42: 9116-9124, (2017).

Arndt, et al., A Critical Assessment of Li/MgO-Based Catalysts for the Oxidative Coupling of Methane, Catalysis Reviews, 53: 424-514, (2011).

Arndt, et al., Mn—Na2WO4/SiO2 as Catalyst for the Oxidative Coupling of Methane: What Is Really Known?, Applied Catalysis A: General, 425-426: 53-61, (2012).

Balakotaiah, et al., Scaling Relations for Autothermal Operation of Catalytic Reactors, Ind. Eng. Chem. Res., (2021).

Borchert & Baerns, The Effect of Oxygen-Anion Conductivity of Metal-Oxide Doped Lanthanum Oxide Catalysts on Hydrocarbon Selectivity in the Oxidative Coupling of Methane, Journal of Catalysis, 168: 315-320, (1997).

Bucher, et al., Stability of the SOFC cathode material (Ba,Sr)(Co,Fe)O3-delta in CO2-containing atmospheres, Journal of The Electrochemical Society, 155: B1218, (2008).

Cheng, et al., C2 Selectivity Enhancement in Chemical Looping Oxidative Coupling of Methane over Mg—Mn Composite Oxygen Carrier by Li-Doping-Induced Oxygen Vacancies, ACS Energy Lett., 3: 1730-1736, (2018).

Cruellas, et al., Oxidative Coupling of Methane in Membrane Reactors: A Techno-Economic Assessment, Processes, 8: 274, (2020).

Cruellas, et al., Advanced Reactor Concepts for Oxidative Coupling of Methane, Catalysis Reviews, 59: 234-294, (2017).

Czuprat, et al., Oxidative Coupling of Methane in a BCFZ Perovskite Hollow Fiber Membrane Reactor, Ind. Eng. Chem. Res., 49: 10230-10236, (2010).

De Jong, et al., Towards Single Step Production of Multi-layer Inorganic Hollow Fibers, Journal of Membrane Science, 239: 265-269, (2004).

Dimitrakopoulos, et al., Highly Durable C2 Hydrocarbon Production via the Oxidative Coupling of Methane Using a BaFe0.9Zr0.1O3?? MIEC Membrane and La2O3 Catalyst, ACS Catal., 11: 3638-3661, (2021).

Farrell, et al., A Viewpoint on Direct Methane Conversion to Ethane and Ethylene Using Oxidative Coupling on Solid Catalysts, ACS Catal., 6: 4340-4346, (2016).

Fleischer, et al., Investigation of Na2WO4/Mn/SiO2 Catalyst Composition in Oxidative Coupling of Methane by Chemical Looping Experiments, Journal of Catalysis, 360: 102-117, (2018).

Gambo, et al., Recent Advances and Future Prospect in Catalysts for Oxidative Coupling of Methane to Ethylene: A Review, Journal of Industrial and Engineering Chemistry, 59: 218-229, (2018).

Gerceker, et al., Methane Conversion to Ethylene and Aromatics on PtSn Catalysts, ACS Catal., 7: 2088-2100, (2017).

Guo, et al., Direct, Nonoxidative Conversion of Methane to Ethylene, Aromatics, and Hydrogen, Science, 344: 616-619, (2014).

Haag, et al., Influence of Oxygen Supply in Catalytic Membrane Reactors for OCM, Catalysis Today, 127: 157-164, (2007).

Horn & Schlögl, Methane Activation by Heterogeneous Catalysis, Catal Lett, 145: 23-39, (2015).

Hou, et al., Structure Sensitivity of La2O2CO3 Catalysts in the Oxidative Coupling of Methane, ACS Catal., (2015).

Huang, et al., Exploiting Shape Effects of La2O3 Nanocatalysts for Oxidative Coupling of Methane Reaction, Nanoscale, 5: 10844-10848, (2013).

Hufenus, et al., Melt-spun Polymer Fibers with Liquid Core Exhibit Enhanced Mechanical Damping, Materials & Design, 110: 685-692, (2016).

Igenegbai, et al., OCM over Hybrid Membrane/Catalyst Centers: Requirements for Lifetime, ACS Energy Lett., 1465-1470, (2019).

Igenegbai, et al., In search of membrane-catalyst materials for oxidative coupling of methane: Performance and phase stability studies of gadolinium-doped barium cerate and the impact of Zr doping, Applied Catalysis B, 230: 29-35, (2018).

Ito, et al., Oxidative Dimerization of Methane over a Lithium-Promoted Magnesium Oxide Catalyst, Journal of the American Chemical Society, 107: 5062-5068, (1985).

Keller & Bhasin, Synthesis of Ethylene via Oxidative Coupling of Methane: I. Determination of Active Catalysts, Journal of Catalysis, 73: 9-19, (1982).

Kiani, et al., Oxidative Coupling of Methane (OCM) by SiO2-Supported Tungsten Oxide Catalysts Promoted with Mn and Na, ACS Catalysis, 9: 5912-5928, (2019).

Kim, et al., Nanoparticle Ex-solution for Supported Catalysts: Materials Design, Mechanism and Future Perspectives, ACS Nano, 15: 81-110, (2021).

Kumar, et al., Correlation of Methane Activation and Oxide Catalyst Reducibility and Its Implications for Oxidative Coupling, ACS Catalysis, 6: 1812-1821, (2016).

Kuo, et al., Evaluation of Direct Methane Conversion to Higher Hydrocarbons and Oxygenates, Catalysis Today, 4: 463-470, (1989).

Li, et al., Asymmetric Dual-phase MIEC Membrane Reactor for Coproduction of Synthesis Gases, International Journal of Hydrogen Energy, 44: 4218-4227, (2019).

Li, et al., Feasibility and Mechanism of Lithium Oxide as Sintering Aid for Ce0.8Sm0.2O? Electrolyte, Journal of Power Sources, 205: 57-62, (2012).

Li, et al., X-ray Tomography-assisted Study of Phase Inversion in Ceramic Hollow Fibers, Journal of Membrane Science, 528: 24-33, (2017).

Liang, et al., Methane Conversion to Syngas in Ce0.8Sm0.2O2−?-Sr2Fe1.5Mo0.5O5+? Dual Phase Membrane, International Journal of Hydrogen Energy, 43: 14478-14485, (2018).

Lin, Inorganic Membranes for Process Intensification: Challenges and Perspective, Ind. Eng. Chem. Res., 58: 5787-5796, (2019).

Lu, Oxygen-permeable Dense Membrane Reactor for the Oxidative Coupling of Methane, Journal of Membrane Science, 170: 27-34, (2000).

Luo, et al., Gas-phase Reaction Network of Li/MgO-Catalyzed Oxidative Coupling of Methane and Oxidative Dehydrogenation of Ethane, ACS Catalysis, (2019).

McFarland, Unconventional Chemistry for Unconventional Natural Gas, Science, 338: 340, (2012).

Olivos-Suarez, et al., Strategies for the Direct Catalytic Valorization of Methane Using Heterogeneous Catalysis: Challenges and Opportunities, ACS Catal., 6: 2965-2981, (2016).

Ormerod, Solid Oxide Fuel Cells, Chem. Soc. Rev., 32: 17-28, (2003).

Othman, et al., A Micro-structured La0.6Sr0.4Co0.2Fe0.8O3?? Hollow Fibre Membrane Reactor for Oxidative Coupling of Methane, Journal of Membrane Science, 468: 31-41, (2014).

(56) References Cited

OTHER PUBLICATIONS

Othman, et al., An Oxygen Permeable Membrane Microreactor with an In-situ Deposited Bi1.5Y0.3Sm0.2O3?? Catalyst for Oxidative Coupling of Methane, Journal of Membrane Science, 488: 182-193, (2015).

Ricote & Bonanos, Enhanced Sintering and Conductivity of Co/Ni-doped Ba Cerate-Zirconate, Solid State Ionics, 181: 694-700, (2010).

Sakbodin, et al., Hydrogen-Permeable Tubular Membrane Reactor: Promoting Conversion and Product Selectivity for Non-Oxidative Activation of Methane over an Fe © SiO2 Catalyst, Angewandte Chemie, 128: 16383-16386, (2016).

Sarkar, et al., Bifurcation Analysis of Oxidative Coupling of Methane in Monolith, Gauze or Wire-Mesh Reactors, Catalysis Today, (2021).

Schucker, et al., The Effect of Strontium Content on the Activity and Selectivity of Sr-Doped La2O3 Catalysts in Oxidative Coupling of Methane, Applied Catalysis A: General, 117827, (2020).

Schwach, et al., Direct Conversion of Methane to Value-Added Chemicals over Heterogeneous Catalysts: Challenges and Prospects, Chem. Rev., 117: 8497-8520, (2017).

Spivey & Hutchings, Catalytic Aromatization of Methane, Chemical Society Reviews, 43: 792-803, (2014).

Stansch, et al., Comprehensive Kinetics of OCM over La2O3/CaO, Ind. Eng. Chem. Res., 36: 2568-2579, (1997).

Tan & Li, Oxidative Coupling of Methane in a Perovskite Hollow-Fiber Membrane Reactor, Ind. Eng. Chem. Res., 45: 142-149, (2006).

Tan, et al., Preparation of LSCF Ceramic Hollow-Fiber Membranes for Oxygen Production, Ind. Eng. Chem. Res., 44: 61-66, (2005).

Taniguchi, et al., Proton Conductive Properties of Gd-Doped Ba Cerates, Solid State Ionics, 53-56: 998-1003, (1992).

Ten Elshof, et al., Oxidative Coupling of Methane in a Mixed-Conducting Perovskite Membrane Reactor, Applied Catalysis A: General, 130: 195-212, (1995).

Vamvakeros, et al., Real Time Chemical Imaging of a Working Catalytic Membrane Reactor During OCM, Chemical Communications, 51: 12752-12755, (2015).

Van Hassel, et al., Oxygen Permeation Flux through La1—ySryFeO3, Applied Catalysis A, 119: 279-291, (1994).

Vandewalle, et al., Mass and Heat Transfer in Novel Reactors for OCM, Chemical Engineering Science, 198: 268-289, (2019).

Wang, et al., Oxidative Coupling of Methane over Oxide-Supported Sodium-Manganese Catalysts, Journal of Catalysis, 155: 390-402, (1995).

Wu, et al., A Novel Dual-Layer Ceramic Hollow Fibre Membrane Reactor for Methane Conversion, Journal of Membrane Science, 352: 63-70, (2010).

Xu & Thomson, Perovskite-type Oxide Membranes for the Oxidative Coupling of Methane, AlChE Journal, 43: 2731-2740, (1997).

Xue, et al., Gas to Liquids : Natural Gas Conversion to Aromatic Fuels and Chemicals in a Hydrogen-Permeable Ceramic Hollow Fiber Membrane Reactor, ACS Catal., 6: 2448-2451, (2016).

Zavyalova, et al., Statistical Analysis of Past Catalytic Data on Oxidative Methane Coupling for New Insights into the Composition of High-Performance Catalysts, ChemCatChem, 3: 1935-1947, (2011).

Zhao, et al., Flower-like Sr—La2O3 Microspheres with Hierarchically Porous Structures for Oxidative Coupling of Methane, Ind. Eng. Chem. Res., 58: 22847-22856, (2019).

Zhu, et al., Electrochemical Conversion of Methane to Ethylene in SOE, Nature Communications, 10: 1173, (2019).

* cited by examiner

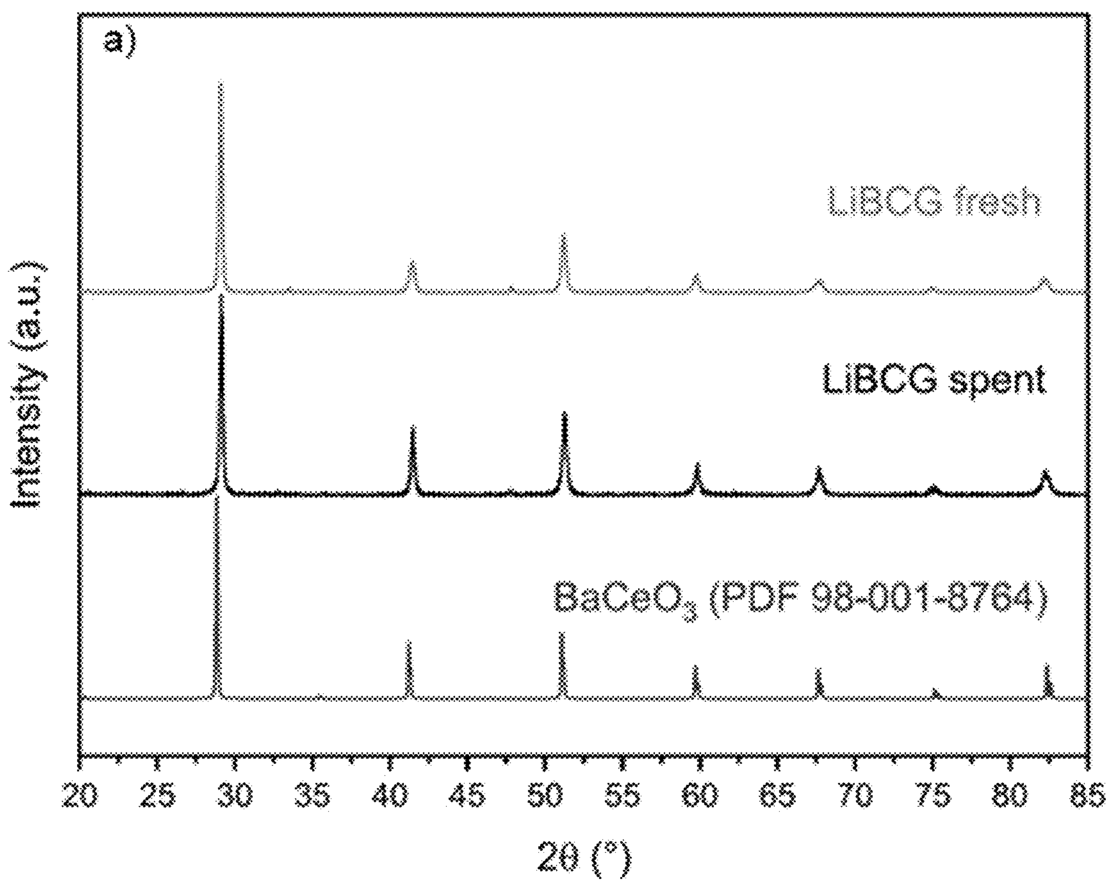
Figure 1A
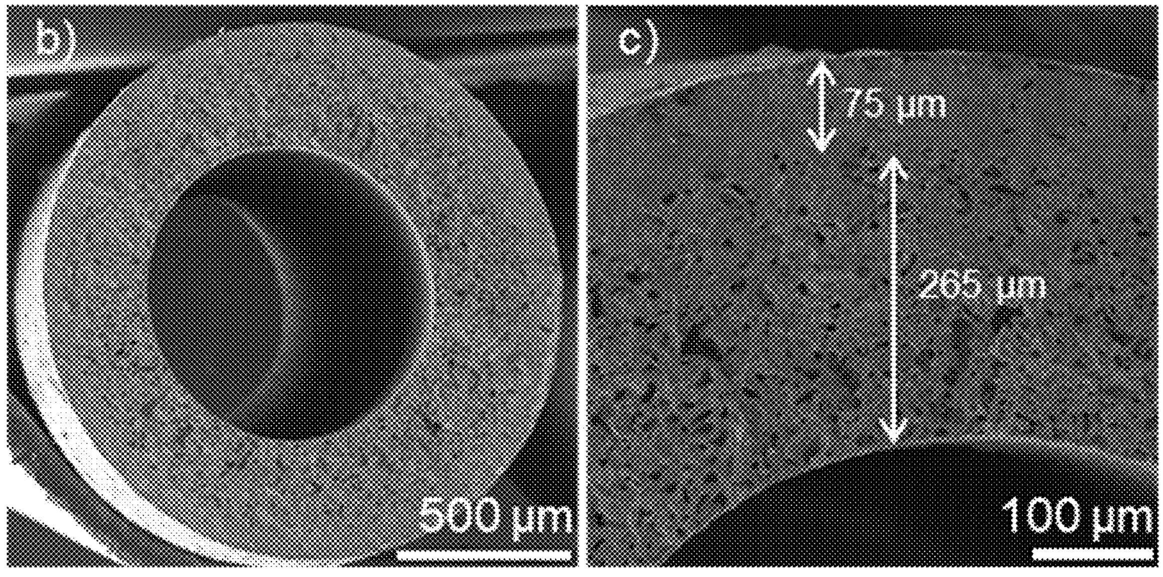
Figure 1B
Figure 1C

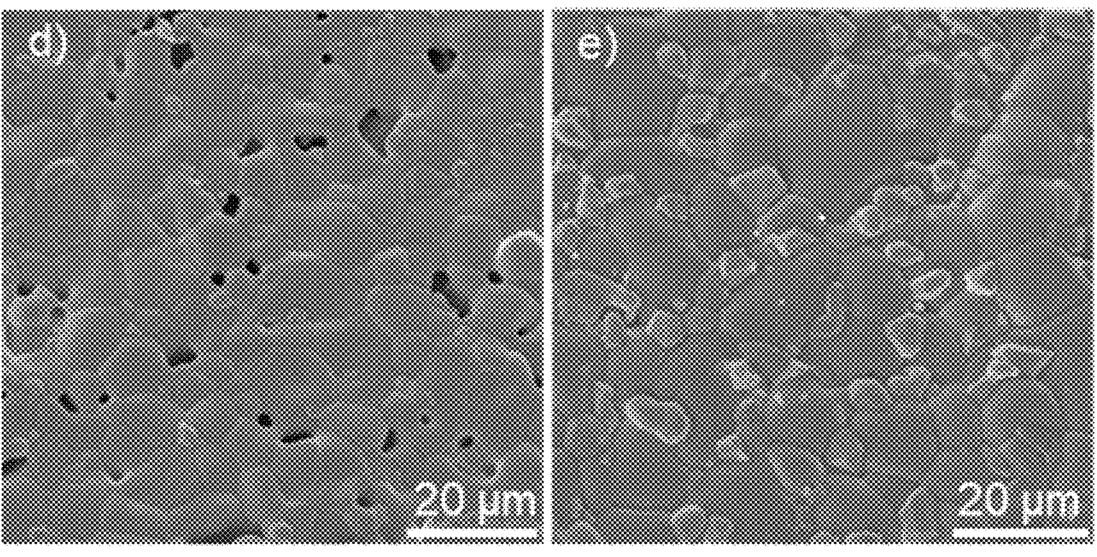
Figure 1D
Figure 1E
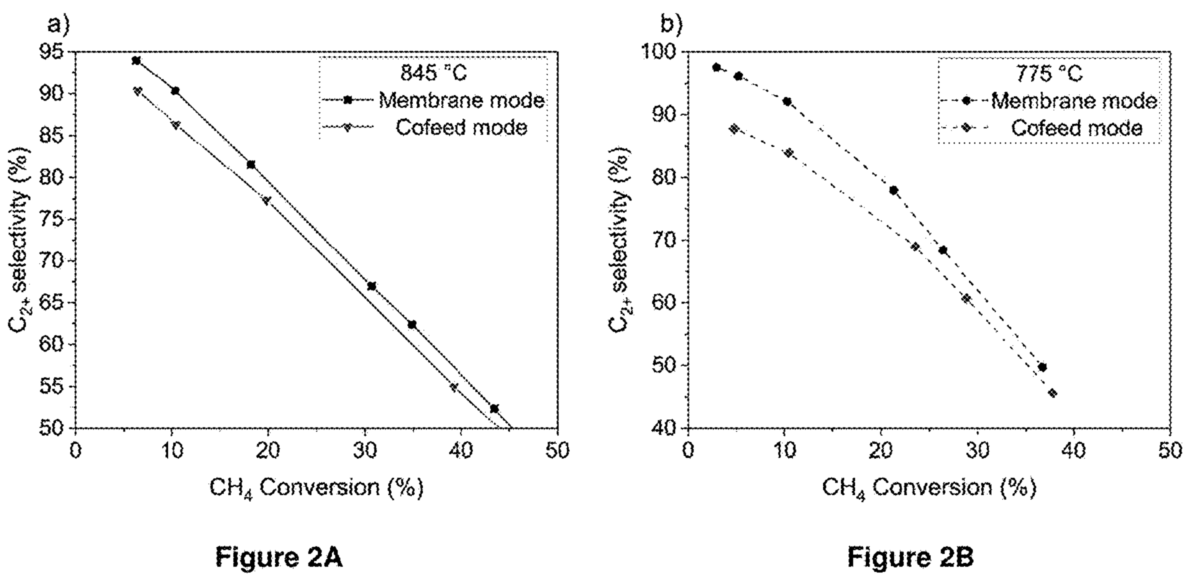
Figure 2A
Figure 2B

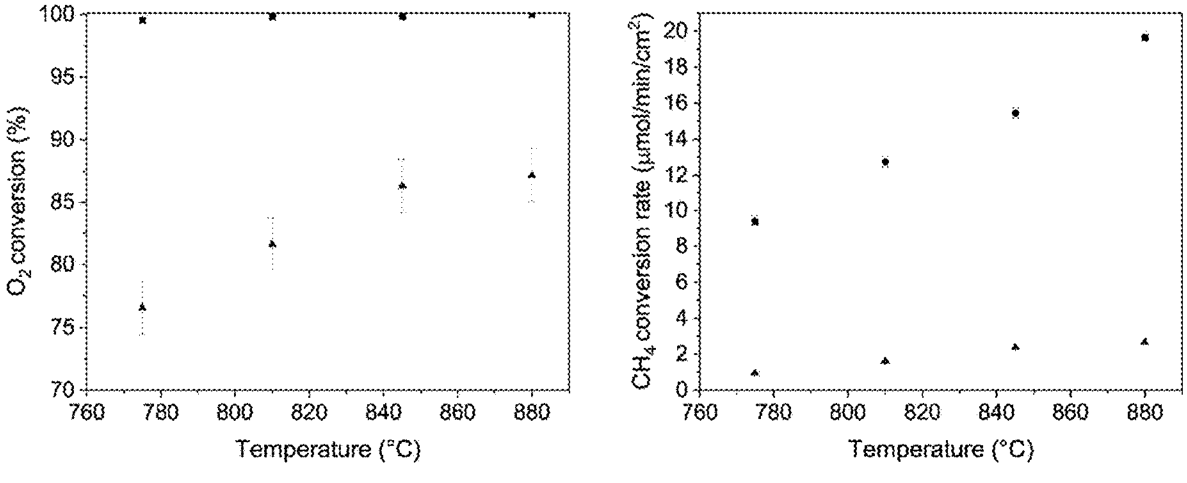
Figure 3C
Figure 3D
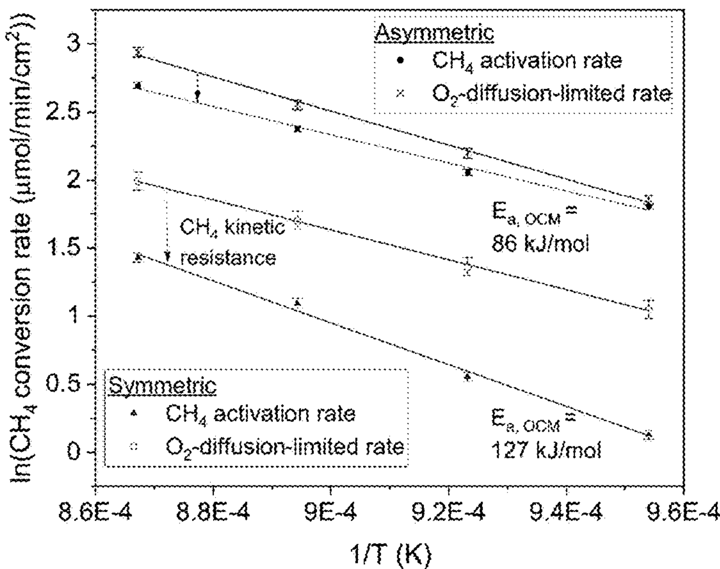
Figure 4

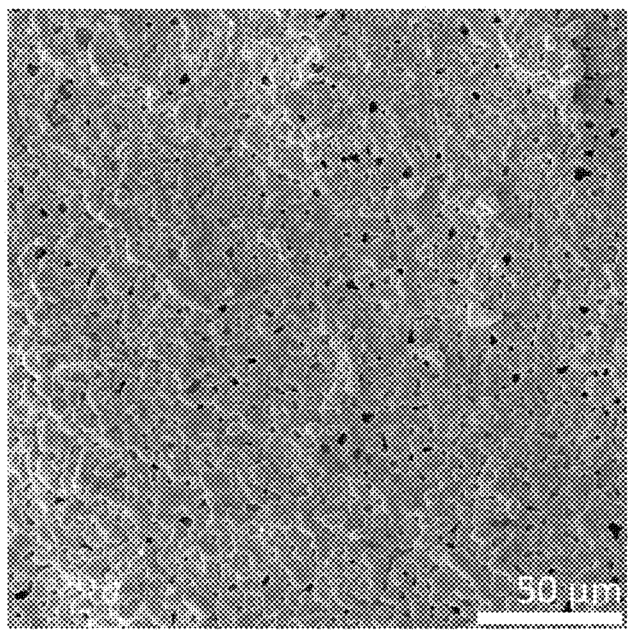
Figure 6
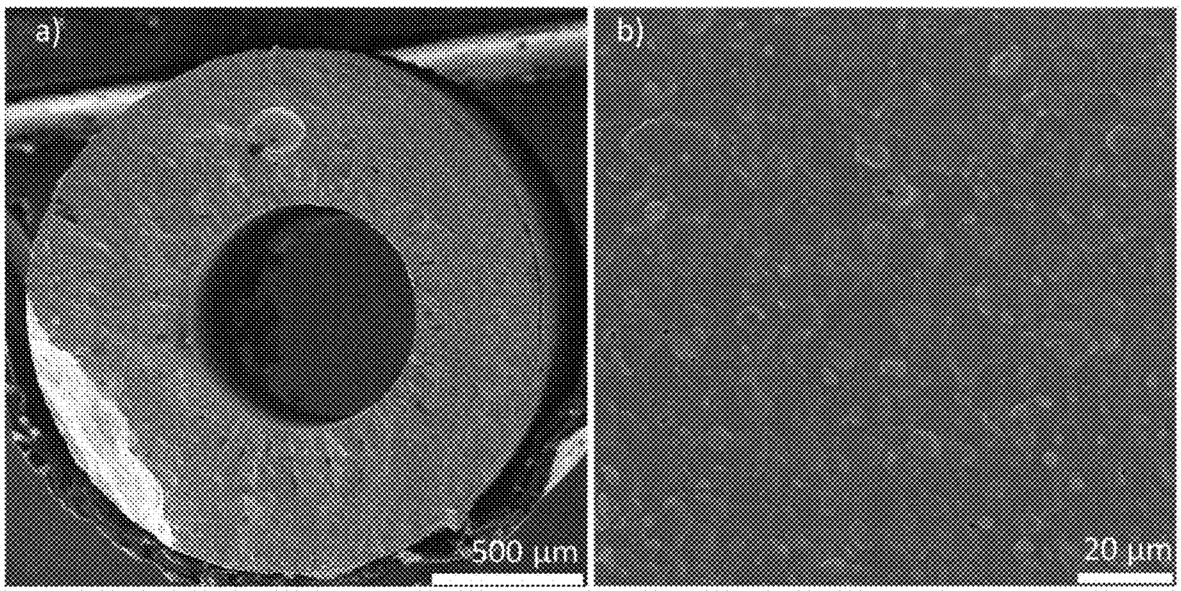
Figure 7A
Figure 7B

DUAL-LAYER HOLLOW FIBER MEMBRANES AND METHODS OF MAKING AND USE

CROSS-REFERENCE TO RELATED APPLICATION

The benefit of priority to U.S. Provisional Patent Application No. 63/344,437 filed May 20, 2022, is hereby claimed and the disclosure is incorporated herein by reference in its entirety.

GOVERNMENT SUPPORT INFORMATION

This invention was made with government support under DE-EE0007888 awarded by the U.S. Department of Energy. The government has certain rights in the invention.

FIELD

The disclosure relates to dual-layer hollow fiber membranes, methods of making the membranes, and methods of using the membranes in oxidative coupling of methane reactions. In particular, the disclosure relates to dual-layer barium-cerium-gadolinium hollow fiber membranes and their method of making and use in oxidative coupling of methane reactions.

BACKGROUND

Established methane-to-chemicals routes rely on indirect, energy-intensive steam reforming, which necessitates production at large scale. In comparison, direct methane conversion processes could possess greater energy and carbon atom efficiency, as well as better suitability for smaller, more remote methane sources. Among thermocatalytic methods, direct methane conversion processes include the oxidative coupling of methane (OCM) to ethylene and other C2+ hydrocarbons, nonoxidative conversion of methane to olefins, aromatics, and H2 (MTOAH), and nonoxidative methane dehydroaromatization to aromatics and H2 (MDA). Among these chemistries, OCM has an advantage of having a negative ΔGrxn and therefore not being limited by an equilibrium conversion. The presence of oxygen, however, inevitably leads to over-oxidation reactions forming CO and $CO_2$ ($CO_x$), which are thermodynamically favored products.

Current OCM catalysts include $Mn/Na_2WO_4/SiO_2$, Li/MgO, and rare earth oxides doped with alkaline or other lower-valent ions (such as $Sr/La_2O_3$) However, even the current vest performing catalysts have not produced as system that can achieve targets such as about 30% $CH_4$ conversion with about 90% $C_{2+}$ selectivity.

SUMMARY

Previous work has shown that homogenous reactions of $O_2$(g) with either $CH_4$ or the $C_{2+}$ products are a detriment to the $C_{2+}$ selectivity and yield. In particular, recent OCM studies have demonstrated the pathways in which $O_2$(g) reacts homogenously with alkyl radicals to yield alkyl peroxide intermediates, which are $CO_x$ precursors. These undesired gas-phase reactions cannot be controlled in conventional packed bed reactor designs where $CH_4$ and $O_2$ are co-fed. Accordingly, reactor designs that decrease or avoid $O_2$(g), such as chemical looping systems or $O_2$—conducting solid oxide membrane reactor systems are predicted to allow for higher $C_{2+}$ selectivity. The central concept behind a membrane reactor design is that by introducing a membrane to transport oxygen to the active catalytic sites, it is possible to enhance the desired product selectivity. In general, this concept has been challenging to implement and optimize since it has been difficult to design membrane reactors where the rate of methane activation at the active site is matched to the rate of oxygen transport through the membrane. The methane activation controls the OCM rate. Any $O_2$ not consumed on the catalyst surface can react with $C_2$ in the gas phase, lowering the selectivity. As a result, conventional membrane reactors have exhibited insufficient $C_{2+}$ selectivity/yield. They also suffer from insufficient stability, low $O_2$ flux, and prohibitively high fabrication cost due to the multiple synthetic steps required.

In contrast to conventional membrane reactors, the hollow fiber membranes of the disclosure have an asymmetric dual-layer hollow fiber geometry with a porous catalyst layer attached to a thin separation layer. The membranes of the disclosure are manufactured using a continuous, simultaneous phase inversion approach, which can provide catalyst layer thickness tunability, allowing for control over the number of active catalytic sites and therefore the rates of $CH_4$ activation within the membrane, which in turn can be beneficial for matching of the flux of oxygen to the reaction rates. The manufacturing process is also simplified as compared to prior processes, requiring only a single sintering step. The hollow fiber geometry can beneficially enable high transport surface areas per volume of reactor, which leads to higher volumetric reactions rates and lower overall reactor volumes. The membranes of the disclosure also have excellent interfacial layer adhesion and mechanical strength. The small diameter of the hollow fibers provides for enhanced heat transfer compared to larger tubes, which is beneficial for improved heat management.

BRIEF DESCRIPTION OF THE DRAWINGS

FIG. 1A is a powder XRD spectra of as-formed (fresh) and spent LiBCG asymmetric hollow fiber membranes in accordance with the disclosure, cross-references to the standard $BaCeO_3$.

FIG. 1B is a scanning electron microscopy (SEM) image of a cross-section of a LiBCG asymmetric hollow fiber membrane in accordance with the disclosure.

FIG. 1C is an enlarged cross-sectional SEM image of the membrane of FIG. 1B.

FIG. 1D is an SEM image of the inner surface of the membrane of FIG. 1B.

FIG. 1E is an SEM image of the outer surface of the membrane of FIG. 1B.

FIG. 2A is a graph showing $CH_4$ conversion/$C_{2+}$ selectivity for membrane mode and cofed mode at 845° C. for a LiBCG asymmetric hollow fiber membrane in accordance with the disclosure.

FIG. 2B is a graph showing $CH_4$ conversion/$C_{2+}$ selectivity for membrane mode and cofed mode at 775° C. for a LiBCG asymmetric hollow fiber membrane in accordance with the disclosure.

FIG. 2C is a graph showing $CH_4$ conversion/$C_{2+}$ yield for membrane mode at 845° C. and 775° C. for a LiBCG asymmetric hollow fiber membrane in accordance with the disclosure.

FIG. 3C is a graph comparing $O_2$ conversion percent as a function of temperature for a LiBCG asymmetric hollow fiber membrane in accordance with the disclosure and a LiBCG symmetric membrane.

FIG. 3D is a graph comparing $CH_4$ conversion rate as a function of temperature for a LiBCG asymmetric hollow fiber membrane in accordance with the disclosure and a LiBCG symmetric membrane.

FIG. 4 is an Arrhenius plot of the observed $CH_4$ activation rate (solid symbols) compared to the theoretical rate limited by oxygen diffusion only (x symbols) for a LiBCG asymmetric hollow fiber membrane in accordance with the disclosure a LiBCG symmetric membrane.

FIG. 6 is an SEM image of the outer surface of a symmetric BCG hollow fiber membrane (without $Li_2CO_3$ sintering aid) after sintering at 1650° C. for 12 hours.

FIG. 7A is an SEM image of a cross-section of a symmetric BCG hollow fiber membrane.

FIG. 7B is an SEM image of the symmetric BCG hollow fiber membrane of FIG. 7A showing the non-porous inner surface morphology.

DETAILED DESCRIPTION

Figures 2D, 2E, 3A, 3B:
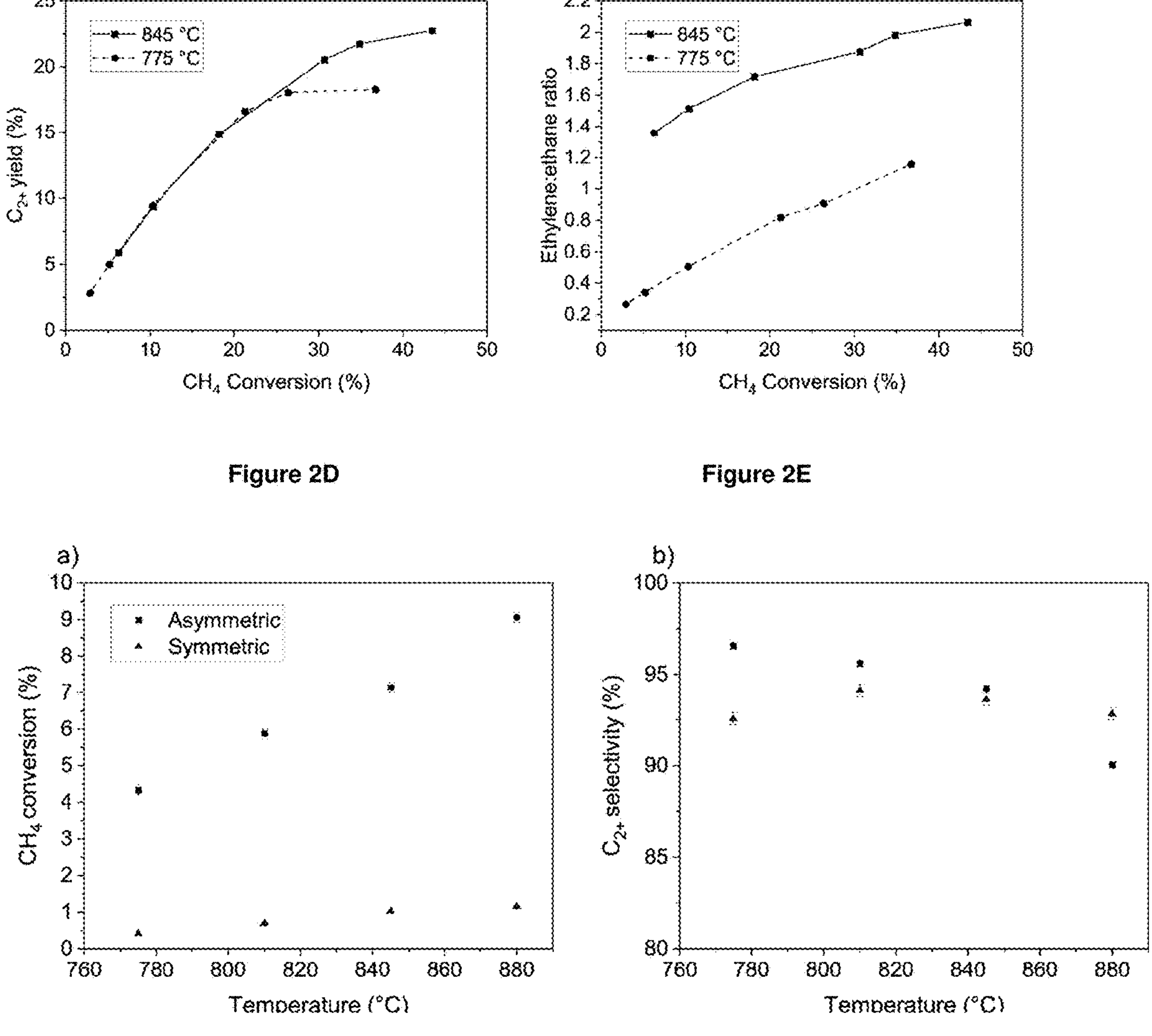
FIG. 2D is a graph showing $CH_4$ conversion/$C_2H_4$:$O_2H_6$ ratios for membrane mode at 845° C. and 775° C. for a LiBCG asymmetric hollow fiber membrane in accordance with the disclosure.
FIG. 2E is a graph showing ethylene:ethane ratio as a function of $CH_4$ conversion for a LiBCG asymmetric hollow fiber membrane in accordance with the disclosure
FIG. 3A is a graph comparing $CH_4$ conversion percent as a function of temperature for a LiBCG asymmetric hollow fiber membrane in accordance with the disclosure and a LiBCG symmetric membrane.
FIG. 3B is a graph comparing $C_{2+}$ selectivity as a function of temperature for a LiBCG asymmetric hollow fiber membrane in accordance with the disclosure and a LiBCG symmetric membrane.

Membranes of the disclosure utilize an asymmetric design outer separation layer and inner porous layer formed of an OCM catalyst. For example, the outer separation layer and inner porous layer can each be formed barium cerate doped with gadolinium (BCG), such as $BaCe_{0.8}Gd_{0.2}O_{3-\delta}$, as a catalyst for OCM and as a membrane for the transport of oxygen. Membranes of the disclosure have been found to have improved selectivity as compared to packed bed reactor systems (using identical catalysts and reactor geometries). Without intending to be bound by theory, it is believed that this improvement is related to a reduction in the rates of non-selective homogenous reactions that involve gas-phase $O_2$ (g). The membranes of the disclosure have been demonstrated to reach $C_{2+}$ yields of up to 22.7%.

Referring to FIG. 1A, the membranes of the disclosure have two distinct concentric layers including an outer separation layer and an inner porous layer. The inner porous layer surrounds an inner bore of the hollow fiber geometry, and the outer separation layer surrounds the inner porous layer. The inner bore has an inner diameter, which corresponds to the inner diameter of the fiber membrane. The hollow fiber membrane can optionally include an inert layer arranged between the outer separation layer and inner porous layer. The inert layer can be used to prevent thermal solid-state reactions between the OCM catalyst and $O^{2-}$ conducting membrane. The inert layer can be formed or and/or include one or more of gadolinium-doped ceria, alumina, and zirconia.

The inner porous layer comprises or is formed of an OCM catalyst material, while the outer separation layer serves as a membrane for transport of oxygen. OCM catalyst materials useful as the inner porous layer, include but are not limited to, BCG, $Mn/Na_2WO_4/SiO_2$, $Bi_{1.5}Y_{0.3}Sm_{0.2}O_{3-x}$ (BYS), $SrO/La_2O_3$, Li/MgO, and combinations thereof. Membrane materials useful as the outer separation layer include, but are not limited to, BCG, $La_{0.6}Sr_{0.4}Co_{0.2}Fe_{0.8}O_{3-x}$ (LSCF), $BaCo_xFe_yZr_z$ (BCFZ, x+y+z=1), $BaFe_{0.9}Zr_{0.1}O_{3-x}$, $Ba_{0.5}Sr_{0.5}Co_{0.8}Fe_{0.2}O_{3-x}$, BSCF—$CeO_{0.8}Gd_{0.2}O_{2-x}$ (BSCF-GDC), and combinations thereof.

For example, the table below lists OCT catalyst materials and membrane materials that can be used in the hollow fiber of the disclosure.

| Catalyst materials (inner porous layer) | Membrane materials (outer separation layer) |
|---|---|
| $Mn/Na_2WO_4/SiO_2$ | $La_{0.6}Sr_{0.4}CO_{0.2}Fe_{0.8}O_{3-x}$ (LSCF) |
| $Bi_{1.5}Y_{0.3}Sm_{0.2}O_{3-x}$ (BYS) | $BaCo_xFe_yZr_z$ (BCFZ, x + y + z = 1) |
| $BaCe_{0.8}Gd_{0.2}O_{3-x}$ (BCG) | $BaFe_{0.9}Zr_{0.1}O_{3-x}$ |
| $SrO/La_2O_3$ | $Ba_{0.5}Sr_{0.5}CO_{0.8}Fe_{0.2}O_{3-x}$ |
| Li/MgO | BSCF-$CeO_{0.8}Gd_{0.2}O_{2-x}$ (BSCF-GDC) |
| BCG | BCG |

For example, each of the inner porous layer and the outer separation layer can include barium cerate doped with gadolinium. For example, they can each include $BaCe_{0.8}Gd_{0.2}O_{3-\delta}$.

An interface is present between the outer separation layer and the inner porous layer. The interface can be substantially free of visible cracks or defects. As used herein "visible cracks or defects" refers to those cracks or defects visible through imaging such as scanning electron microscopy imaging.

The inner porous layer has a thickness as defined from the outer circumferential edge of the inner bore to the interface. The outer separation layer has a thickness as defend from the interface to the outer circumferential edge of the hollow fiber membrane. The inner porous layer is thicker than the outer separation layer.

The inner porous layer has an interconnected pore structure. The presence of the interconnected pore structure can advantageously increase the surface area for methane activation and surface catalysis. For example, the inner porous layer can have a porosity of up to 30%. The membranes of the disclosure can have a well-defined and controlled pore structure. For example, the pores can be relatively uniform in size and shape throughout the layer. The pores can have a circular shape, for example. As compared to conventional methods of forming porous membranes, the pores of the membranes of the disclosure have a more regular circular shape. Conventional fibers generally have a cylindrical shape or fingerlike structures that vary in size and shape in the radial direction as a result of the extrusion process. Use of the triple orifice spinneret as detailed below can allow for improved control, uniformity, and/or tunability of the porous structure of the inner porous layer, including both size and shape of the pores. The pore structure can have an open and accessible pore structure.

The outer separation layer can be non-porous. The outer separation layer can be substantially gas tight. The outer separation layer can be substantially free of defects or other open porosity.

The membranes of the disclosure can have an outer diameter of about 0.5 mm to about 3 mm, about 0.5 mm to about 1 mm, about 1 mm to about 3 mm, or about 1.5 mm to about 2.5 mm. Other suitable outer diameters include about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3 mm.

The membranes of the disclosure can have an inner diameter of about 0.3 mm to about 2.5 mm, about 0.3 mm to about 2.4 mm, about 0.5 mm to about 2 mm, about 1 mm, to about 2.4 mm, or about 0.3 mm to about 1 mm. Other suitable inner diameters include about 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, and 2.5 mm.

The inner porous layer can have a thickness of about 250 μm to about 1.3 mm, about 300 μm to about 1 mm, about 800 μm to about 1.3 mm, about 200 μm to about 350 μm. Other suitable thicknesses can include about 250, 300, 350, 400, 450, 500, 550, 600, 650, 700, 750, 800, 850, 900, 950, 1000, 1100, 1200, and 1300 μm.

The outer separation layer can have a thickness of about 5 μm to about 100 μm, about 10 μm to about 80 μm, about 20 μm to about 60 μm, or about 50 μm to about 100 μm. Other suitable thicknesses include, about 5, 6, 7, 8, 9, 10, 20, 30, 40, 50, 60, 70, 80, 90 and 100 μm.

The membranes of the disclosure have an asymmetric design. The asymmetric design allows for matching of the flux of oxygen through the outer separation membrane layer to the methane activation rate (reaction rate) at the inner porous layer. Flux of oxygen to reaction rates at the catalyst can be matched through tailoring of the diameters of the outer and inner layers, as well as the porosity of the inner layer. For example, the relative diameters of the inner and outer layers and the porosity of the inner layer can be selected such that an oxygen transport rate through the outer layer is substantially the same as a methane reaction rate at the inner porous layer.

It has been surprisingly and beneficially found that this flux matching significantly improves performance of the hollow fiber membrane. This is contrary to expectations with conventional technologies, in which the selection of each layer focused on selecting the best individually performing layers. As detailed below, the hollow fiber membranes of the disclosure demonstrated increase $C_{2+}$ selectivity, which is believed to be attributable to the matching of the flux of oxygen to the reaction rate, which lead to the direction of oxygen atoms to participate in surface-induced OCM reactions, as opposed to driving gas-phase deep oxidation reactions.

The membranes of the disclosure can be formed by co-extrusion of the inner porous and separation layers in a phase inversion process, followed by co-sintering. This additive manufacturing process has reduced processing time and complexity as compared to convention membrane synthesis processes. Further, the additive manufacturing process of the disclosure can allow for improved control over the surface morphology of the inner porous layer. The process of the disclosure can also beneficially allow for membranes with thin outer separation layers to be produced. This can beneficially improve the flux, which limits conventional membrane applicability.

Methods of the disclosure include co-extruding a porous layer precursor suspension, a separation layer precursor suspension, and an internal coagulant through a spinneret into a water bath under conditions to cause phase inversion and solidification of the suspensions to form a precursor fiber. The spinneret includes three orifices. Use of a three-orifice spinneret has been beneficially found to allow improved control over the porous layer formation and resulting pore structure. The co-extrusion is conducted such that the internal coagulant is flowed through the innermost orifice, the separation layer precursor suspension is flowed through the outermost orifice, and the porous precursor layer suspension is flowed through the orifice between the inner and outermost orifices. This results in a structure such that the resulting desired hollow fiber structure is defined by the co-extrusion, with the internal coagulant orifice defining the inner bore, the porous layer precursor suspension orifice defines the inner porous layer, and the separation layer precursor suspension orifice defining the outer separation layer. An air gap of about 0.5 mm to about 2 mm between the spinneret tip and the water bath can be used.

The flow rate of the porous layer precursor suspension, the separation layer precursor suspension, and the internal coagulant during co-extrusion is tunable depending on a desired thickness of the respective inner porous layer and outer separation layer. For example, the porous layer precursor suspension can be injected at a flow rate of about 1.0 ml/min while the separation layer precursor suspension is injected at a flow rate of about 0.4 ml/min. The internal coagulant can be injected at substantially the same flow rate as the porous layer precursor, for example about 1.0 ml/min. Relative flow rates can include, for example, injection of the porous layer suspension at a range of about 10 units/min, with injection of the separation layer suspension at a rate of about 1 unit/min to about 10 units/min and the coagulant at a range of about 4 units/min to about 12 units/min. Other suitable rates and relative rates can be determined by the skilled person to achieve desired layer thicknesses. Syringe pumps can be used to control the flow rates of the suspensions and the internal coagulants. For example, high force syringe pumps such as NE-8000, New Era Pump Systems can be used and were used in the described examples herein.

After the phase inversion process, the precursor fiber is solidified. For example, the precursor fiber can be solidified by soaking in an aqueous solution saturated in the sintering aid included in BCG precursors included in the suspensions to prevent dissolution of the sintering aid until fully solidified. For example, the precursor fiber can be soaked in an aqueous solution containing $Li_2CO_3$. For example, the membranes can be soaked for about 8 hours to about 24 hours.

The solidified precursor fiber can then be dried, for example at a temperature of about 20° C. to about 100° C., about 50° C. to about 100° C., or about 25° C. to about 75° C. Any suitable drying time can be used and adjusted based on the temperature. For example, the solidified membranes can be dried at about 100° C. for 2 hours. For example, vacuum drying could be used, which could accommodate faster drying times and/or lower temperatures.

The dried precursor fiber can then be sintered at about 1600° C. to about 1700° C. to convert the precursors to the final BCG membrane composition, thereby forming the asymmetric hollow fiber membrane having an inner porous layer surrounded by an outer separation layer. It has been surprisingly found that the separation layer forming a substantially gas tight layer along with a porous layer could be co-sintered while forming the desired BCG phase. The dried precursor fiber can be sintered within a sacrificial bath of BCG precursor powder. This can avoid excessive barium evaporation during sintering. Sintering can be performed with a ramp rate of about 1° C./min when heating and about 2° C./min when cooling. Controlled organic burnout can be performed during sintering with dwells at 475° C. and 700° C. This can aid in minimizing defects.

Both the separation layer precursor suspension and the porous layer precursor suspension include BCG precursor. The BCG precursor includes stoichiometric amounts of $BaCO_3$, $CeO_2$, and $Gd_2O_3$, and optionally a sintering aid. For example, the BCG precursor can include stoichiometric amounts such that upon sintering the barium cerate doped with gadolinium formed is $BaCe_{0.8}Gd_{0.2}O_{3-\delta}$. For example, $Li_2CO_3$ can be included as the sintering aid. Other sintering aids can include, for example, NiO, CuO, and ZnO. It has been surprisingly found that $Li_2CO_3$ can be used as a sintering aid with the solid-state reactive sintering process of the invention. The expectation in the art was that $LiCO_3$ would not allow for the BCG phase to form along with the dense layer needed as the separation layer in a co-sintering process. $LiCO_3$ is a beneficial sintering aid because it does not adversely affect the OCM reaction process as it is generally expected to evaporate during the sintering process. Any $LiCO_3$ that may remain could be beneficial in the OCM reaction process. The sintering aid can be included in an amount of about 0.5 wt % to about 2 wt %. The BCG precursor can be prepared by combining the components and ball-milling in ethanol. The milled powder can be sifted to remove large aggregates. For example, the milled powder can be sifted with a sieve selected such that the resulting powder includes particles having an average particle size of less than 75 μm.

The porous layer precursor suspension includes the BCG precursor, a pore forming additive, a solvent, a polymer, and a phase inversion additive. The separation layer precursor suspension includes the BCG precursor, a solvent, a polymer, and a phase inversion additive.

The pore forming additive can be, for example, graphite. Polymers soluble in the solvent may be also usable. The pore forming additive can be provided in an amount of about 5 wt % to about 30 wt %, about 10 wt % to about 20 wt %, about 5 wt % to about 15 wt %, or about 8 wt % to about 25 wt %, based on the total weight of the porous layer precursor suspension. Other suitable pore forming additive amounts based on the total weight of the porous layer precursor suspension include about 5, 6, 7, 8, 9, 10, 12, 14, 16, 18, 20, 22, 24, 26, 28, and 30 wt %.

In the porous layer precursor suspension and/or the separation layer precursor suspension, the solvent can be, for example, dimethylsulfoxide (DMSO), n-methyl pyrrolidone (NMP), and/or dimethylformamide (DMF). The solvent can be provided in an amount of about 20 wt % to about 40 wt %, about 25 wt % to about 35 wt % or about 30 wt % to about 40 wt % based on the total weight of the respective suspension. Other suitable amounts can include based on the total weight of the respective suspensions about 20, 22, 24, 26, 28, 30, 32, 34, 36, 38, and 40 wt %.

In the porous layer precursor suspension and/or the separation layer suspension, the polymer can be, for example, polyethersulfone (PES) and/or cellulose acetate. The polymer can be provided in an amount of about 4 wt % to about 10 wt %, about 5 wt % to about 8 wt %, or about 6 wt % to about 10 wt % based on the total weight of the respective suspension. Other suitable amounts based on the total weight of the respective suspension include about 4, 5, 6, 7, 8, 9, and 10 wt %.

In the porous layer precursor suspension and/or the separation layer precursor suspension, the phase inversion additive can be polyvinylpyrrolidone (PVP). The phase inversion additive can be provided in an amount of about 0.1 wt % to about 3 wt %, about 0.5 wt % to about 1 wt %, or about 1 wt % about 3 wt % based on the total weight of the respective suspension. Other suitable amount based on the total weight of the respective suspension include about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3 wt %.

The internal coagulant can be water, polyvinyl alcohol, or a combination thereof. For example, the internal coagulant can be a mixture of water and polyvinyl alcohol. For example, the mixture can include about 0 wt % to about 30 wt % PVA and about 70 wt % to about 100 wt % water. The use of an aqueous PVA solution as the internal coagulant was found to improve extrusion reproducibility by ensuring concentricity of the extruded layers. It was also found to enlarge the bore region of the fiber compared to the use of DI water alone.

The membranes of the disclosure are capable of improved OCM performance as compared to conventional membranes. The membranes can be used for converting methane to target products such as ethylene and other $C_{2+}$ hydrocarbons through oxidative coupling of methane. The membrane is exposed to a methane containing source in the presence of oxygen. The inner porous layer catalyzes the oxidative coupling of methane reaction while the outer separation layer is a membrane for the transport of oxygen to the inner porous layer. The method can be performed with oxygen being fed at $O^{2-}$ through the membrane or by feeding $O_2$ g) with the methane containing source.

The OCM reaction can be performed at a temperature of about 700° C. to about 900°, about 775° C. to about 880° C., or about 750° C. to about 850° C.

The membranes of the disclosure can achieve a 65% $O_{2+}$ selectivity with 30% $CH_4$ conversion. Beneficially the membranes of the disclosure can result in greater than 0.2 mL of desired product forming per minute per $cm^2$ of membrane.

The OCM performance under different $CH_4$ conversion levels was tested by using dilution of $CH_4$ in $N_2$ at a constant lumen flow rate of 5 mL STP/min. Dilution of $CH_4$ with $N_2$ increases the ratio of permeated $O_2$ to fed $CH_4$, increasing the $CH_4$ conversion. Maintaining the lumen flow rate at 5 mL/min, rather than simply decreasing the flow rate of an undiluted $CH_4$ stream, was chosen because it eliminates differences in reactor dead volume times and residence time distributions.

To understand the positive effect of membrane mode operation on the $C_{2+}$ selectivity, a membrane in accordance with the disclosure was tested in two different oxygen delivery modes: oxygen fed as $O^{2-}$ through the membrane (membrane mode) and oxygen fed as $O_2$(g) at the inlet alongside methane (cofeed mode). In these two separate modes, the total flow rate of 5 mL/min was maintained, and the variation in $CH_4$ concentration in $N_2$ was identical. The amount of $O_2$ cofed was adjusted to match the $O_2$ permeation in membrane mode. This amount of cofed $O_2$ remained constant for each point along the conversion/selectivity curve, while the methane in the stream became more dilute.

FIGS. 2A and 2B show the $CH_4$ conversion/$C_2$, selectivity curves for the LiBCG asymmetric hollow fiber membranes of the disclosure at 845° C. and 775° C., respectively. By comparing the $C_{2+}$ selectivity at a given $CH_4$ conversion between membrane and cofeed modes, it was observed that the benefit of utilizing $O^{2-}$ rather than $O_2$(g) as an oxygen source was about a 5-10% increase in selectivity. The membrane mode performance at 845° C. had a $C_{2+}$ selectivity of 67.0% was measured at 30.7% $CH_4$ conversion. The inner surface porosity of the membranes of the disclosure is conducive to activating the surface with additional deposited catalyst, which may further increase $CH_4$ conversion rate and $C_{2+}$ selectivity.

Figures 8, 9:
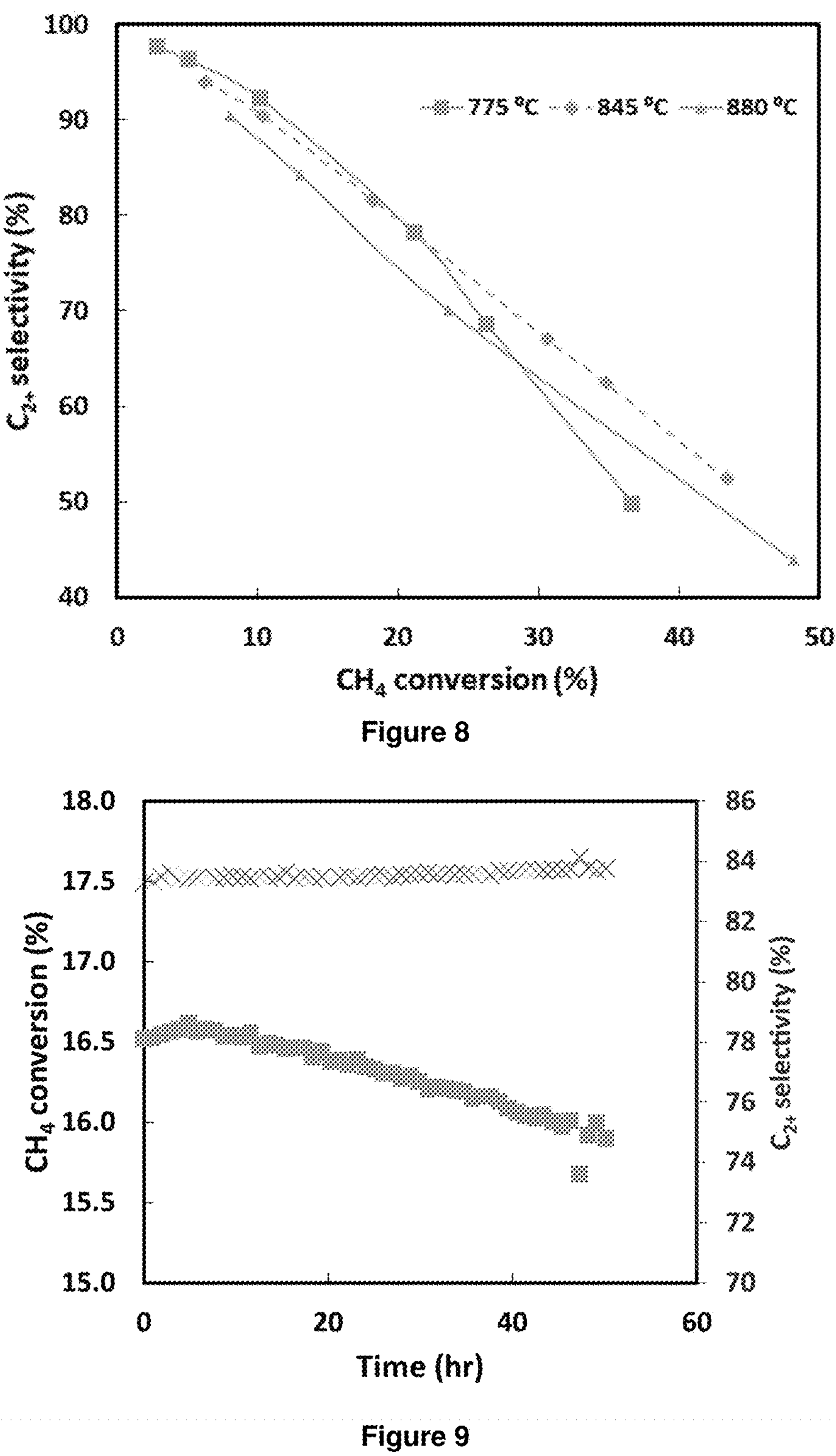
FIG. 8 is a graph showing a comparison of $CH_4$ conversion/$C_2$ selectivity of a membrane in accordance with the disclosure for different OCM operating temperature.
FIG. 9 is a graph showing $CH_4$ conversion/$C_2$ selectivity stability test for membrane mode operation of a fiber in accordance with the disclosure at conditions of 845° C., 5 mL/min of 19% $CH_4$ feed (remainder inert) in the lumen side, 200 mL/min air on the shell side.

The membrane mode $C_{2+}$ yields are shown in FIG. 2C. At 845° C., a maximum $C_{2+}$ yield of 22.7% (14.8% $C_2H_4$ yield) was achieved at 43.4% $CH_4$ conversion, although the $C_{2+}$ selectivity was only 52.4% at these conditions. This is over a 40% improvement from a previous report of 16% maximum $C_{2+}$ yield in a symmetric BCG membrane reactor. Lu, Y. Oxygen-permeable dense membrane reactor for the oxidative coupling of methane. *Journal of Membrane Science* 170, 27-34 (2000). When operating at $CH_4$ conversions below 25%, the $C_{2+}$ yield curve at 775° C. appeared similar to 845° C. However, at higher $CH_4$ conversions, the selectivity was higher at 845° C. than at 775° C. The conversion/selectivity curve at 880° C. (shown in FIG. 8) showed lower selectivity at low conversions. This decline may indicate that thermal decomposition of $CH_4$ or $C_{2+}$ to form carbon, followed by deposit oxidation to form $CO_x$, is beginning to contribute at these temperatures. An additional consideration is the $C_2H_4$:$C_2H_6$ ratio, since $C_2H_4$ is more desirable. Although increased $CH_4$ conversion always led to higher $C_2H_4$:$C_2H_6$ ratio, as can be seen in FIG. 2D, the ratio was also increased by operating at higher temperatures. Without intending to be bound by theory, it is believed that this is due to increased homogeneous ethane dehydrogenation rates. For the LiBCG hollow fiber tested, the data indicates that the optimal operating temperature was around near 845° C.

Referring to FIG. 5, the stability of the OCM performance was evaluated for 50 hours at 845° C. The $CH_4$ conversion decreased from 16.5% to 15.9% over the course of the test, with a corresponding slight increase in the $C_{2+}$ selectivity. Previous studies have suggested that deactivation of BCG under OCM conditions occurs as a result of phase segregation into $BaCO_3$ and $CeO_2$ phases, especially in the presence of $CO_2$. Zr doping has been shown to increase the phase stability of BCG and other similar materials and may optionally be used herein.

Figure 5A:
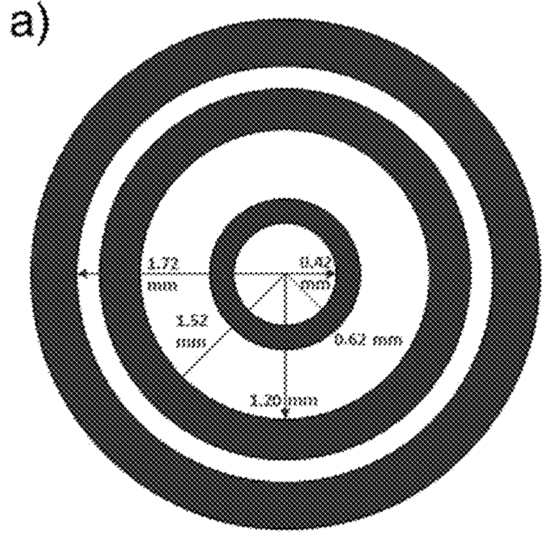
FIG. 5A is a schematic illustration of a spinneret with orifice diameters for making an asymmetric hollow fiber membrane in accordance with the disclosure.
Figure 5B:
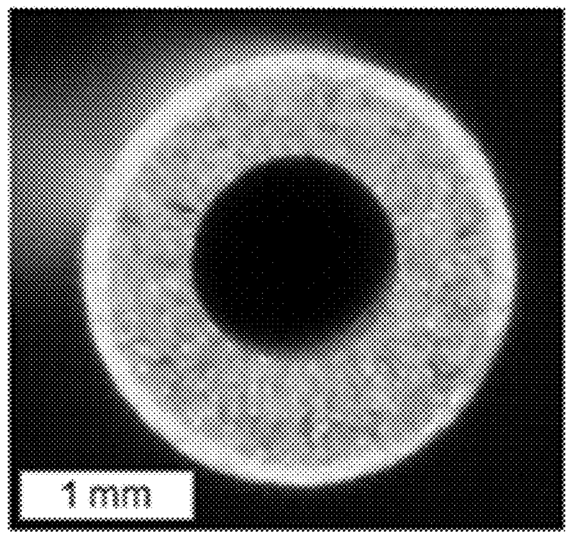
FIGS. 5B and 5C are cross-sectional optical images of a precursor fiber formed in accordance with the methods of the disclosure.
Figure 5C:
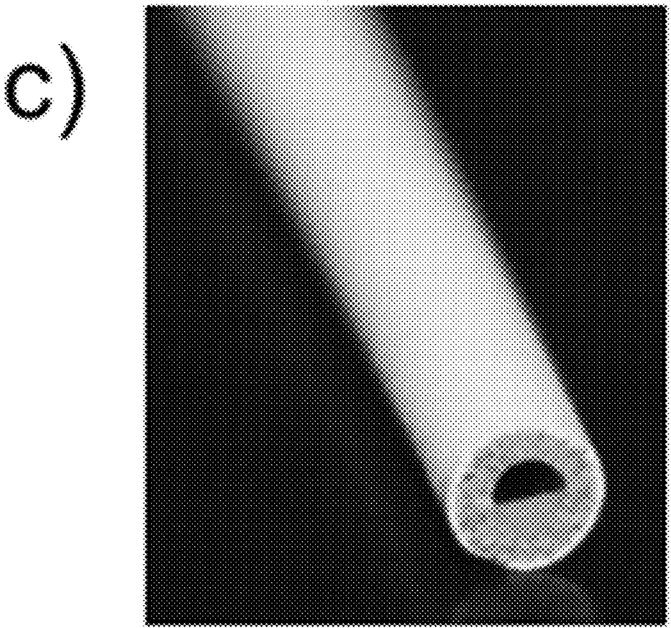
Figure 5D:
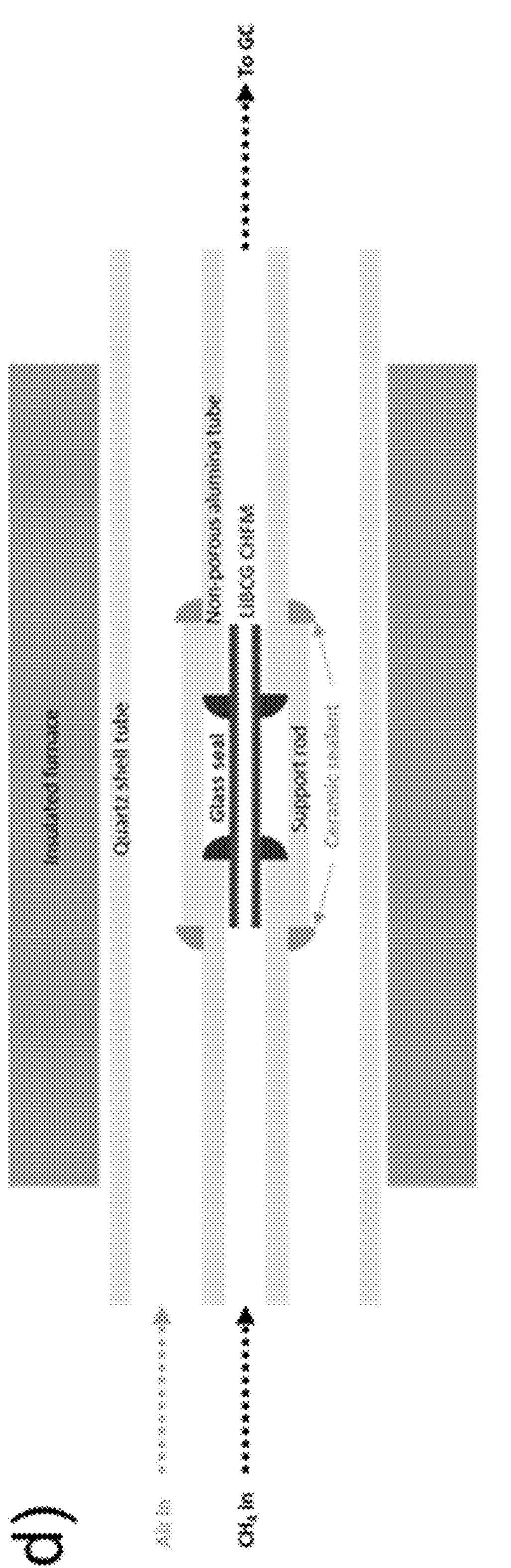
FIG. 5D is a schematic illustration of a reactor set-up for use of a membrane in an OCM reaction in accordance with the disclosure.

As shown in FIG. 2, the hollow fiber membranes of the disclosure can achieve excellent $C_{2+}$ selectivity and yield. Performance benefits were observed by matching the heterogeneous OCM rate to the $O_2$ permeation rate. This was evaluated by comparing the fiber membranes of the disclosure to a control experiment using a typical LiBCG symmetric hollow fiber of the same length. The synthesis parameters for the symmetric fibers are shown in Table 2 in the Examples below. FIG. 7 shows a cross-sectional SEM image of the symmetric membrane, which had an average separation layer thickness of 470 microns. The symmetric membrane had a nonporous inner layer, which does not allow for controlling the catalyst surface area. The control experiment was useful in examining the effects of the inner porous layer of the fiber membrane of the disclosure. FIG. 5C shows the testing setup used.

Referring to FIG. 3, the asymmetric fiber in accordance with the disclosure achieved a $CH_4$ conversion that was approximately an order of magnitude higher than the symmetric control fiber. Given that the fibers had similar diameters and exposed length, it is believed that the increase in $CH_4$ conversion is attributable to the increase in the $O_2$ flux. Without intending to be bound by theory, it is believed that the increase in $O_2$ flux was due to the thinner separation layer and the increased surface area for $O_2$ and $CH_4$ consumption, which leads to increase $C_{2+}$ selectivity for the asymmetric membranes of the disclosure was greater or comparable to the symmetric control membranes at the temperature range of interest (775° C.≤T≤845° C. It was expected in the art that an increase in conversion of $CH_4$ results in a decrease in the $C_{2+}$ selectivity. Contrary to this expectation, the fiber membranes in accordance with the disclosure did not exhibit the decreased $C_{2+}$ selectivity.

Referring to FIGS. 3A and 3B, it is believed that the increased surface area of the porous catalyst layer served to increase the $C_{2+}$ selectivity at a given conversion level.

Without intending to be bound by theory, the observed increase in the $C_{2+}$ selectivity in the asymmetric fiber membranes of the disclosure compared to the symmetric control fiber was due to a decrease in the rate of evolution of gas phase $O_2$ compared to the heterogeneous OCM rate. This would lead to the direction of the oxygen atoms to participate in surface-induced OCM reactions as opposed to driving gas-phase deep oxidation reactions. This theory was supported by the measurements of the $O_2$ conversion, which showed that for the asymmetric fiber membrane of the disclosure, the conversion of the $O_2$ that transferred through the membrane was above 99% at all temperatures. In contrast, for the symmetric control membrane, the $O_2$ conversion was only 75-85%. That is, a large amount of the permeated oxygen in the symmetric membrane evolved into $O_2$(g) rather than being consumed by the OCM surface reaction. At these temperatures, homogenous oxidation of the $O_{2+}$ products can lower selectivity substantially. The trend of increasing $O_2$ conversion with increasing temperature indicates the relative ease of activating $CH_4$ at higher temperatures.

Figure 10:
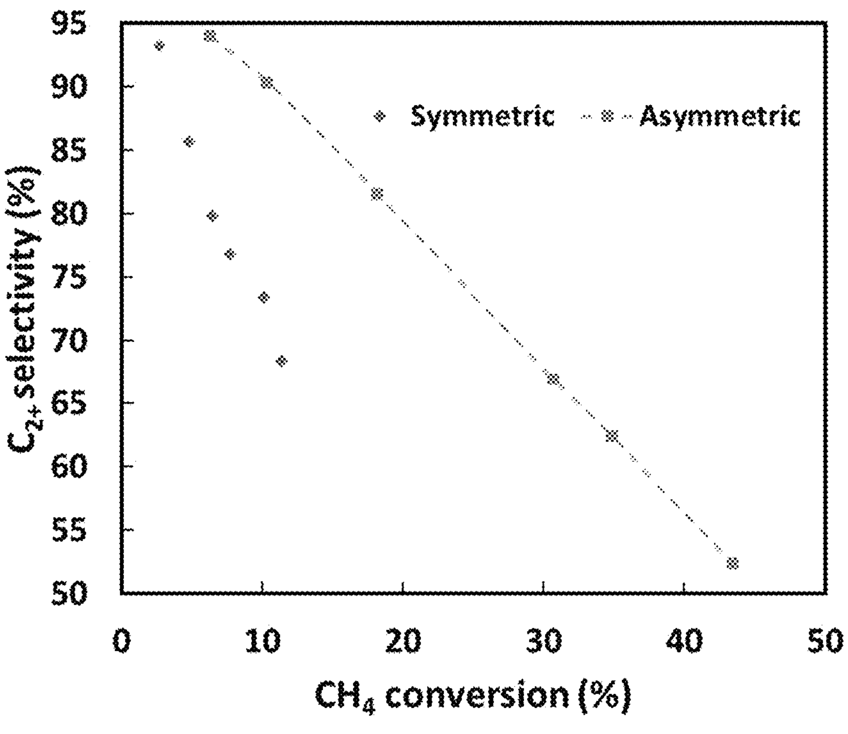
FIG. 10 is a graph showing a comparison of $CH_4$ conversion/$C_2$ selectivity at 845° C. for a LiBCG asymmetric hollow fiber membrane in accordance with the disclosure and a symmetric LiBCG fiber membrane.

Referring to FIG. 10, the conversion/selectivity curve at 845° C. for the symmetric fiber membrane high $C_{2+}$ selectivity was observed at $CH_4$ conversion under 5%, but the selectivity fell below 70% at just 10% conversion.

A framework for understanding the different pathways for consumption of oxygen was developed. The desired reactions of $O^{2-}$ are the abstraction of H from $CH_4$ to form $\cdot CH_3$, and the oxidative dehydrogenation of $C_2H_6$ to form $C_2H_4$. Some surface oxidation of $\cdot CH_3$ and the $C_{2+}$ products to form $CO_x$ is unavoidable. However, another pathway to $CO_x$ is through the recombination of $O^{2-}$ into $O_2$(g), which will lead to decreased $C_{2+}$ selectivity due to homogeneous $C_{2+}$ oxidation. It has been suggested in earlier publications that $O_{2-}$ recombination limits $C_{2+}$ selectivity. However, it is difficult to quantify $O^{2-}$ recombination under OCM conditions because $O_2$(g) can quickly be consumed by homogenous reactions. To minimize $O_2$(g) in OCM dense membrane reactor systems, the rate of selective H abstraction from $CH_4$ (generally considered to be the rate determining step in OCM) should match as closely as possible with the rate of $O^{2-}$ diffusion. It was assumed that overall $CH_4$ activation rate is limited by two resistances in series: 1) the resistance associated with abstracting H from $CH_4$ on the oxygen-lean membrane side, and 2) the "oxygen diffusion resistance", a resistance which is the sum of resistances from bulk oxygen diffusion kinetics and oxygen dissociation kinetics on the oxygen-rich side of the membrane.

The balance between these two major resistances to target molecule activation has previously been described as a dimensionless Biot number (Bi), where the rate of heterogeneous oxidation on the membrane surface was divided by the oxygen diffusion rate. Small Bi indicates a membrane reactor where oxygen flux is limited mostly by the surface oxidation step. A small Bi would also be favorable for $O_2(g)$ evolution, which would lower $C_{2+}$ selectivity through homogeneous oxidation.

$$Bi = \frac{\text{heterogeneous } CH_4 \text{ activation rate}}{\text{oxygen diffusion rate through membrane}}$$

Figure 11:
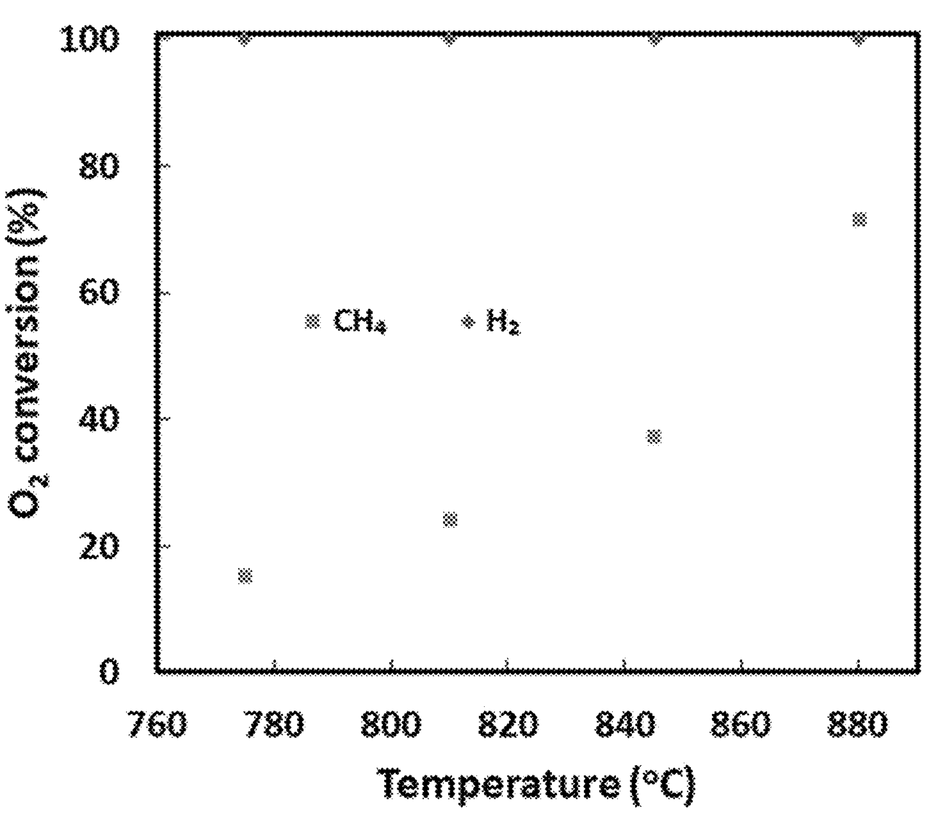
FIG. 11 is a graph showing a comparison of $O_2$ conversion for blank reactor with similar gas-phase residence time as a methane fiber membrane reactor. Conditions were 1 mL/min air cofed with 9 mL/min of either $CH_4$ or $H_2$ into a quartz tube with a 4 mm inner diameter.

$CH_4$ is generally difficult to activate due to its strong C—H bonds, low polarizability, high LUMO and low HOMO. This means that Bi is likely low in OCM membrane reactor systems, especially when the catalytic OCM rate or catalyst surface area is insufficient. In contrast, $H_2$ is very easily activated at these temperatures, so Bi should be relatively high compared to the OCM case. Therefore, the case of $H_2$ oxidation acts as a useful benchmark in qualitatively assessing the value of Bi in OCM dense membrane reactor systems. The assumption of easy $H_2$ activation at these temperatures was verified by measuring homogeneous $O_2$ conversion of $H_2/O_2$ and $CH_4/O_2$ in a cofed blank quartz reactor, which is shown in FIG. 11.

To illustrate the effect of the inner porous catalyst layer on the Biot number, the rate of $CH_4$ activation was compared to the rate of $O^{2-}$ consumption by $H_2$. The maximum theoretical $CH_4$ activation rate was defined by multiplying the $O_2$ flux under $H_2$ oxidation conditions by 4, accounting for the number of $CH_4$ molecules activated by one molecule of $O_2$ according to the stoichiometry of the primary desired OCM step:

$$2\ CH_4 + \frac{1}{2} O_2 \rightarrow C_2H_6 + H_2O$$

$O_2$ flux under $H_2$ oxidation conditions can be thought of as an upper bound for the $O_2$ flux, limited only by the oxygen diffusion resistance and not by C—H bond breaking resistance. Adjusting for stoichiometry converts this flux to a maximum $CH_4$ activation rate that could be achieved if C—H bond breaking in $CH_4$ presented no resistance to the overall membrane reactor rate.

This study was carried out for both asymmetric in accordance with the disclosure and symmetric control membranes in the temperature range of 775° C.≤T≤880° C. The results are shown in FIG. 4 in the form of an Arrhenius plot, where the maximum theoretical $CH_4$ oxidation rate (limited only by the oxygen diffusion resistance) is compared to the observed $CH_4$ oxidation rate (limited by both C—H bond breaking resistance and the oxygen diffusion resistance).

The data from FIG. 4 shows that the asymmetric design has increased both the $CH_4$ activation rate and the $H_2$ activation rate. Focusing on the two symmetric series in FIG. 4, it is clear that C—H bond activation strongly limits the overall reaction rate in the system: the observed $CH_4$ activation rate is much lower than the oxygen diffusion limited rate. In contrast, the oxygen diffusion limited rate and the observed $CH_4$ activation rate are quite similar for the asymmetric case. This suggests that the inner porous catalyst layer has resulted in the surface oxidation kinetics more closely matching the oxygen diffusion kinetics, i.e., the Biot number is closer to unity for the asymmetric case. This is consistent with the improvement in $C_{2+}$ selectivity membranes of the disclosure as shown in FIG. 3; the porous catalyst layer decreases the amount of $O_2(g)$ that reacts homogeneously with the $C_{2+}$ products to form $CO_x$.

EXAMPLES

Example 1 Manufacture of Membranes $BaCO_3$(Alfa Aesar, 99.8%), $CeO_2$ (Alfa Aesar, 99.9%), $Gd_2O_3$ (Alfa Aesar, 99.9%), and $Li_2CO_3$ (Acros Organics, 99+%) were used to synthesize LiBCG membranes via solid-state reactive sintering. Graphite (Alfa Aesar, 325 mesh, 99%) was used as a pore former for the porous inner layer. Dimethylsulfoxide (Sigma-Aldrich, anhydrous, >99.9%), polyethersulfone (PES-BASF, Ultrason E 6020 P), and polyvinylpyrrolidone (PVP-Sigma-Aldrich, M.W.=55000), were used as solvent, polymer, and additive for the phase inversion process, respectively. DI water and a 27 wt % solution of polyvinyl alcohol (88% hydrolyzed, M.W.=20000-30000, Acros Organics) in DI water were used as external and internal coagulants, respectively.

Dual-layer asymmetric hollow fiber membranes were synthesized using a co-extrusion and co-sintering technique in accordance with the disclosure. BCG precursor powders were synthesized by ball-milling (Retsch PM100) stoichiometric amounts of $BaCO_3$, $CeO_2$, and $Gd_2O_3$ in ethanol for 24 hours, with 1 wt % $Li_2CO_3$ added as a sintering aid. After sifting the particles to below 75 μm to ensure the absence of large aggregates, the powders were then mixed with DMSO/PES/PVP into suspensions having the compositions in Table 1, below. The suspensions were sonicated for 2 hours for homogenization/degassing, followed by loading the suspensions into stainless steel syringes. The syringes were then degassed in a vacuum chamber for 1 hour.

TABLE 1

Co-Extrusion Synthesis Parameters for the Asymmetric LiBCG Membrane in accordance with the disclosure

| | Porous layer | Separation layer | Internal coagulant |
|---|---|---|---|
| Composition (wt %) | | | |
| BCG precursor | 50.9 | 63.7 | — |
| Graphite | 12.7 | — | — |
| DMSO | 28.0 | 28.0 | — |
| PES | 6.4 | 6.4 | — |
| PVP | 2.0 | 2.0 | — |
| PVA | — | — | 27.0 |
| Water | — | — | 73.0 |
| Flow rate (mL/min) | 1.0 | 0.4 | 1.0 |

To synthesize dual-layer membrane precursors, suspensions were coextruded through a triple-orifice spinneret into a water bath causing phase inversion and solidification of the suspensions. FIG. 5A is an illustration of the spinneret dimensions used. During the phase inversion process, high-force syringe pumps (NE-8000, New Era Pump Systems)

were used to accurately control flow rates of suspensions and internal coagulant. An air gap of 1 mm between the spinneret tip and the water bath was used. The other synthesis parameters are shown in Table 1. A 27 wt % polyvinyl alcohol (PVA) aqueous solution was used as the internal coagulant. PVA internal coagulant, instead of DI water alone, offered greater extrusion reproducibility. In previous reports, a large viscosity mismatch between internal coagulants (like water) and viscous dope solution has been shown to create extrusion instabilities. Changing to aqueous PVA coagulant increased the reproducibility of CHFM co-extrusion by ensuring concentricity of the distinct layers. It also enlarged the bore region of the fiber compared to DI water alone.

For the symmetric LiBCG fiber of the comparative example, the spinneret dimensions and synthesis parameters are in Table 2.

TABLE 2

Spinneret dimensions and synthesis parameters for symmetric LiBCG CHFMs

| | Separation layer | Internal coagulant |
|---|---|---|
| Composition (wt %) | | |
| BCG precursor | 63.7 | — |
| DMSO | 28.0 | — |
| PES | 6.4 | — |
| PVP | 2.0 | — |
| PVA | — | — |
| Water | — | 100 |
| Flow rate (mL/min) | 0.3 | 0.2 |
| Needle outside radius (mm) | 1.88 | 0.62 |
| Needle inside radius (mm) | 1.50 | 0.42 |

After the phase inversion process, the membranes were left to fully solidify for 24 hours in an aqueous solution saturated with $Li_2CO_3$ to prevent dissolution of the sintering aid. The membranes were straightened and dried at 100° C. for 2 hours. Optical images of the membrane precursors are shown in FIGS. 5B-5C. The final membrane was obtained using sintering at 1650° C. for 12 hours. The membranes were sintered within a sacrificial bath of BCG precursor powder, to avoid excessive barium evaporation during sintering. The ramp rate was 1° C./min when heating and 2° C./min when cooling. The sintering program also included controlled organic burnout dwells at 475° C. and 700° C. for 2 hours, to minimize defects.

To distinguish the effect of $Li_2CO_3$ on the sintering temperature of BCG, the microstructure of a hollow fiber prepared using the same sintering conditions but without $Li_2CO_3$ is shown in FIG. 6. It is clear that $Li_2CO_3$ incorporation lowered the sintering temperature of the LiBCG CHFMs. Previous studies have suggested that $Li_2O$, a decomposition product of $Li_2CO_3$, enables sintering temperature reduction via a liquid phase sintering mechanism. Given the high volatility of lithium species at the final 1650° C. sintering temperature, the lithium was not expected to be present in the final membranes.

Examples 2 Reaction Testing

To test the OCM performance of the membranes of the disclosure and the comparative symmetrical membranes, the membranes were loaded into a reactor set-up as illustrated in FIG. 5C. A glass sealant was used to form a gas-tight seal between the membranes and two non-porous alumina tubes. When quantifying the length and area of the tested membrane sections, the portion covered by glass sealant was not included in the length. A ceramic adhesive and multiple alumina rods were used to fix the alumina tubes together without exerting mechanical stress on the hollow fibers. This entire combination was placed into a quartz tube and heated to 900° C. at 1° C./min in flowing air to finish curing the seal, then cooled to reaction temperature. The inner diameter of the non-porous alumina tube was only 2.38 mm, which decreased reactor dead volume. The data in FIG. 2 are for a membrane with exposed length of 2.0 cm. The data in FIG. 3 are for two membranes (one symmetric, one asymmetric) each having a length of 1.8±0.1 cm. The lengths do not include the portions of the membrane where 02 permeation was prevented by the glass sealant.

Mass flow controllers (Cole-Parmer) were used to meter the flow into the shell and lumen sides of the hollow fiber membrane reactor. All flow rates referenced herein are in units of mL STP/min. The reactor effluent was analyzed using an Agilent 7890B gas chromatograph (GC) containing two thermal conductivity detectors (one for helium and hydrogen, one for $CO_2$, CO, $O_2$ and $N_2$) and a flame ionization detector (for hydrocarbons). Unless otherwise mentioned, an ice water trap was used to prevent water condensation inside the GC sample loop. For each unique data point, the values are an average of three separate GC trials, and the error bars shown are the sample standard deviation of the three runs. Within a data series, the largest standard deviation was used as the error bar for the whole series. The GC method allowed for reproducibility within ±0.1% for $CH_4$ conversion and ±0.3% for $C_2$, selectivity.

Before beginning the OCM reaction, He sweep gas (>99.999%) was introduced to the lumen side while maintaining 200 mL/min air sweep gas on the shell side. The $O_2$ flux from leaking ($J_{O_{2,leak}}$) was calculated based on the amount of $N_2$ that permeated to the lumen side. For the symmetric and asymmetric membranes, >95% and >99% of the $O_2$ was a result of ionic conduction, respectively.

For OCM experiments, a mixture of 95% $CH_4$ and 5% He (as an internal standard) with <100 ppm impurities was fed to the lumen side, sometimes diluted with $N_2$ (>99.999%), for a total flow of 5 mL/min. Air was fed into the shell side at a flow rate of 200 mL/min. During cofed control experiments, 200 mL/min of $N_2$ was fed on the shell side, while 0.1 mL/min of air was cofed on the lumen side with varying amounts of $CH_4$ and $N_2$ for a total flow rate of 5 mL/min. The equations for $CH_4$ conversion, $CH_4$ conversion rate, $C_{2+}$ selectivity, $C_{2+}$ yield, $O_2$ flux and $O_2$ conversion are described in detail below. The carbon balance in all experiments was between 98 and 100%. A hydrogen balance comparing fed $CH_4$ to remaining $CH_4$ and the $C_2$, products was used to calculate the effluent mole fraction of water vapor that would have been present if an ice bath were not used.

For $O_2$ flux ($J_{O_2}$) measurements under $H_2$ oxidation conditions, the lumen flow rate was kept at a higher level (20 mL/min of 95% $H_2$) to prevent water condensation, the ice trap was removed, and a thermohygrometer (Cole-Parmer) was used to measure water formation. When comparing this data to OCM, a flow rate of 20 mL/min 95% $CH_4$ was used. The equation for $J_{O_2}$ is found in the SI. For both $CH_4$ conversion rate and $J_{O_2}$, the surface area was defined by the outer surface area (exposed to the air side).

Example 3 Membrane Characterization

X-ray diffraction (XRD) was used to examine the crystalline phases of the fresh and spent membranes made in accordance with Example 1 and tested in accordance with Example 2. XRD was performed with a Rigaku MiniFlex 600 using Cu Kα (λ=1.54059 Å) radiation source at 40 kV/15 mA. The scan speed was 2° (2θ) per minute and the step width was 0.02°. The dense membrane samples were finely ground in a mortar and pestle before XRD characterization.

Scanning electron microscopy was used to analyze the morphologies of the synthesized membranes, and to estimate the thickness of the distinct layers. SEM was performed using a TESCAN MIRA3 at 15 kV accelerating voltage.

Example 4 Equations for Membrane Reactor Experiments

The following equations were used to describe the membrane performance. For OCM experiments, the total molar flow rate from the reactor effluent was calculated using the 5% He standard. $N_x$ denotes the flow rate of species x in μmol/min.

$$X_{CH_4}(\%) = \frac{100[2(N_{C_2H_4}+N_{C_2H_6})+3(N_{C_3H_6}+N_{C_3H_8})+N_{CO}+N_{CO_2})]]}{\text{moles of } CH_4 \text{ fed}} \tag{1}$$

$$X_{CH_4} \text{ rate } (\mu\text{mol cm}^{-2}\text{ min}^{-1}) = \frac{X_{CH_4}N_{total}}{A_{outer}} \tag{2}$$

$$S_{C_{2+}}(\%) = \frac{[2(N_{C_2H_4}+N_{C_2H_6})+3(N_{C_3H_6}+N_{C_3H_8})]}{\text{moles of } CH_4 \text{ consumed}} \times 100 \tag{3}$$

$$Y_{C_{2+}}(\%) = \frac{S_{C_2} \cdot X_{CH_4}}{100} \tag{4}$$

$$X_{O_2}(\%) = \left(1 - \frac{\mu\text{mol } O_2 \text{ min}^{-1} \text{ left in effluent}}{J_{O_2} * A_{outer}}\right) * 100 \tag{5}$$

$$J_{O_2} \text{ for } OCM\ (\mu\text{mol cm}^{-2}\text{ min}^{-1}) = \frac{0.5 * N_{H_2O} + 0.5 * N_{CO} + N_{CO_2}}{A_{outer}} \tag{6}$$

$$J_{O_2} \text{ for } H_2 \text{ oxidation } (\mu\text{mol cm}^{-2}\text{ min}^{-1}) = \frac{0.5 * N_{H_2O}}{A_{outer}} \tag{7}$$

Modifications and other embodiments disclosed herein will come to mind to one skilled in the art to which the disclosed compositions and methods pertain having the benefit of the teachings presented in the foregoing descriptions. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

It is also to be understood that the terminology used herein is for the purpose of describing particular aspects only and is not intended to be limiting. As used in the specification and in the claims, the term "comprising" can include the aspect of "consisting of." Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The use of the terms "a," "an," "the," and similar referents in the context of the disclosure herein (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure herein and is not a limitation on the scope of the disclosure herein unless otherwise indicated. No language in the specification should be construed as indicating any non-claimed element as essential to the practice of the disclosure herein.

ASPECTS OF THE DISCLOSURE

Aspect 1. An asymmetric hollow fiber membrane for oxidative coupling of methane, comprising:

- an inner bore having an inner diameter;
- an inner porous layer surrounding the inner bore, the inner porous layer having an interconnected network of pores defined therein; and
- an outer separation layer surrounding the inner porous layer, the outer separation layer being substantially non-porous, wherein
- the inner porous layer comprises an oxidative coupling of methane (OCM) catalyst and the outer separation layer comprises a membrane for oxygen separation and transport through the outer separation layer,
- the inner porous layer has a thickness as measured from an outer circumferential edge of the inner bore to an interface between the inner porous layer and the outer separating layer;
- the outer separation layer has a thickness as measured from the interface to an outer circumferential edge of the hollow fiber membrane, and
- the thickness of the inner porous layer is greater than the thickness of the outer separation layer and a relative thicknesses of the inner porous layer and outer separation layer and a porosity of the inner porous layer are selected such that a rate of transport of oxygen through the outer separation layer substantially equals a rate of methane activation at the inner porous layer.

Aspect 2. The membrane of claim 1, wherein the inner porous layer comprises one or more of BCG, $Mn/Na_2WO_4/SiO_2$, $Bi_{1.5}Y_{0.3}Sm_{0.2}O_{3-x}$ (BYS), $SrO/La_2O_3$, and Li/MgO.

Aspect 3. The membrane of claim 1 or 2, wherein the outer separation layer comprises one or more of BCG, $La_{0.6}Sr_{0.4}Co_{0.2}Fe_{0.8}O_{3-x}$ (LSCF), $BaCo_xFe_yZr_z$ (BCFZ, x+y+z=1), $BaFe_{0.9}Zr_{0.1}O_{3-x}$, $Ba_{0.5}Sr_{0.5}Co_{0.8}Fe_{0.2}O_{3-x}$ (BSCF), and $CeO_{0.8}Gd_{0.2}O_{2-x}$ (BSCF-GDC).

Aspect 4. The membrane of any one of the preceding claims, further comprising an inert layer arranged between the inner porous layer and the outer separation layer.

Aspect 5. The membrane of claim 1, wherein both the inner porous layer and the outer separation layer are formed of barium doped gadolinium (BCG).

Aspect 6. An asymmetric hollow fiber membrane for oxidative coupling of methane, comprising:

an inner bore having an inner diameter;

an inner porous layer surrounding the inner bore, the inner porous layer having an interconnected network of pores defined therein; and an outer separation layer surrounding the inner porous layer, the outer separation layer being substantially non-porous, wherein the inner porous layer and the outer separation layer each comprise barium cerate doped with gadolinium, the inner porous layer has a thickness as measured from an outer circumferential edge of the inner bore to an interface between the inner porous layer and the outer separating layer;

the outer separation layer has a thickness as measured from the interface to an outer circumferential edge of the hollow fiber membrane, and the thickness of the inner porous layer is greater than the thickness of the outer separation layer.

Aspect 7. The membrane of aspect 5 or 6, wherein the barium cerate doped with gadolinium is $BaCe_{0.8}Gd_{0.2}O_{3-\delta}$.

Aspect 8. The membrane of any one of the preceding aspects, wherein the outer diameter of the membrane is about 0.5 mm to about 3 mm.

Aspect 9. The membrane of any one of the preceding aspects, wherein the inner diameter of the membrane is about 0.3 mm to about 2.5 mm.

Aspect 10. The membrane of any one of the preceding aspects, wherein the thickness of the inner porous layer is about 250 μm to about 1300 μm.

Aspect 11. The membrane of any one of the preceding aspects, wherein the thickness of the outer separation layer is about 5 μm to about 100 μm.

Aspect 12. The membrane of any one of the preceding aspects, wherein the interface is substantially free of visible cracks and/or defects.

Aspect 13. The membrane of any one of the preceding aspects, wherein the inner porous layer has a porosity of up to about 30%.

Aspect 14. A method of converting methane to a target product comprising ethylene and/or other $C_{2+}$ hydrocarbons through oxidative coupling of methane, comprising exposing the membrane of any one of the preceding aspects to a methane containing source in the presence of oxygen, wherein the inner porous layer catalyzes an oxidative coupling of methane reaction, and the outer separation layer is a membrane for the transport of oxygen to the inner porous layer.

Aspect 15. The method of aspect 14, wherein the oxygen is fed as $O^{2-}$ through the membrane.

Aspect 16. The method of aspect 14, wherein the oxygen is fed at $O_2(g)$ with the methane containing source.

Aspect 17. The method of any one of aspects 14 to 16, wherein the method is performed at a temperature of about 700° C. to about 900° C.

Aspect 18. The method of any one of aspects 14 to 17, wherein the 02+ selectivity is at least about 65% for a $CH_4$ conversion of at least 30%.

Aspect 19. The method of any one of aspects 14 to 18, wherein greater than about 0.2 mL of target product is formed per minute per $cm^2$ of membrane.

Aspect 20. A method of making an asymmetric hollow fiber membrane, comprising:

co-extruding a porous layer precursor suspension, a separation layer precursor suspension and an internal coagulant to form a precursor fiber, wherein the suspensions undergo a phase inversion process;

solidifying the precursor fiber; and sintering the precursor fiber to form the asymmetric hollow fiber, wherein:

the porous layer precursor suspension comprises a BCG precursor, a solvent, a polymer, a pore forming additive, and a phase inversion additive, the separation layer precursor suspension comprises the BCG precursor, a solvent, a polymer, and a phase inversion additive, the BCG precursor comprises stoichiometric amounts of $BaCO_3$, $CeO_2$, and $Gd_2O_3$ such that upon sintering a barium cerate doped with gadolinium is formed, and the hollow fiber comprises an inner porous layer comprising the barium cerate doped with gadolinium and an interconnected network of pores surrounding an inner bore, and an outer separation layer comprising the barium cerate doped with gadolinium surrounding the inner porous layer.

Aspect 21. The method of aspect 20, wherein the e BCG precursor comprises stoichiometric amounts of $BaCO_3$, $CeO_2$, and $Gd_2O_3$ such that upon sintering the barium cerate doped with gadolinium is $BaCe_{0.8}Gd_{0.2}O_{3-\delta}$.

Aspect 22. The method of aspect 20 or 21, wherein the BCG precursor further comprises a sintering aid.

Aspect 23. The method of aspect 22, wherein the sintering aid is one or more of $Li_2CO_3$, NiO, CuO, and ZnO.

Aspect 24. The method of aspect 23, wherein the sintering aid is $Li_2CO_3$.

Aspect 25. The method of any one of aspects 22 to 24, wherein the sintering aid is present in the BCG precursor in an amount of about 0.5 wt % to about 2 wt % based on the total weight of the BCG precursor.

Aspect 26. The method of any one of aspects 22 to 25, wherein the precursor fiber is solidified in an aqueous solution comprising the sintering aid.

Aspect 27. The method of any one of aspects 20 to 26, wherein the precursor fiber is sintered in a sacrificial bath comprising the BCG precursor.

Aspect 28. The method of any one of aspects 20 to 27, wherein the pore forming additive is graphite.

Aspect 29. The method of any one of aspects 20 to 28, wherein the pore forming additive is present in an amount about 5 wt % to about 30 wt % based on the total weight of the porous layer precursor suspension.

Aspect 30. The method of any one of aspects 20 to 29, wherein the solvent in the porous layer precursor suspension and/or the separation layer precursor suspension is one or more of dimethylsulfoxide (DMSO), n-methyl pyrrolidone (NMP), and dimethylformamide (DMF.

Aspect 31. The method of any one of aspects 20 to 30, wherein the solvent is present in the porous layer precursor suspension and/or the separation layer precursor suspension about 20 wt % to about 40 wt % based on the total weight of the respective one of the porous layer precursor suspension or the separation layer precursor suspension.

Aspect 32. The method of any one of aspects 20 to 31, wherein the polymer in the porous layer precursor suspension and/or the separation layer precursor suspension is polyethersulfone (PES) and/or cellulose acetate.

Aspect 33. The method of any one of aspects 20 to 32, wherein the polymer is present in the inner porous layer precursor suspension and/or the separation layer precursor suspension about 4 wt % to about 10 wt % based on the total weight of the respective one of the inner porous layer precursor suspension or the separation layer precursor suspension.

Aspect 34. The method of any one of aspects 20 to 33, wherein the phase inversion additive in the porous layer precursor suspension and/or the separation layer precursor suspension is polyvinylpyrrolidone (PVP).

Aspect 35. The method of any one of aspects 20 to 34, wherein the phase inversion additive is present in the porous layer precursor suspension and/or the separation layer precursor suspension about 0.1 wt % to about 3 wt % based on the total weight of the respective one of the porous layer precursor suspension or the separation layer precursor suspension.

Aspect 36. The method of any one of aspects 20 to 35, wherein the internal coagulant comprises one or more of water and polyvinyl alcohol.

Aspect 37. The method of aspect 36, wherein the internal coagulant comprises both water and polyvinyl alcohol.

Aspect 38. The method of aspect 37, wherein the water is present in an amount of about 70 wt % to about 100 wt % based on the total weight of the internal coagulant and the PVA is present in an amount of about 0 wt % to about 30 wt % based on the total weight of the internal coagulant.

Aspect 39. The method of any one of aspects 20 to 38, wherein the coextrusion is performed through a triple orifice spinneret.

REFERENCES

1. Horn, R. & Schlögl, R. Methane Activation by Heterogeneous Catalysis. *Catal Lett* 145, 23-39 (2015).
2. McFarland, E. Unconventional Chemistry for Unconventional Natural Gas. *Science* 338, 340 (2012).
3. Schwach, P., Pan, X. & Bao, X. Direct Conversion of Methane to Value-Added Chemicals over Heterogeneous Catalysts: Challenges and Prospects. *Chem. Rev.* 117, 8497-8520 (2017).
4. Olivos-Suarez, A. I. et al. Strategies for the Direct Catalytic Valorization of Methane Using Heterogeneous Catalysis: Challenges and Opportunities. *ACS Catal.* 6, 2965-2981 (2016).
5. Zavyalova, U., Holena, M., Schlögl, R. & Baerns, M. Statistical Analysis of Past Catalytic Data on Oxidative Methane Coupling for New Insights into the Composition of High-Performance Catalysts. *ChemCatChem* 3, 1935-1947 (2011).
6. Gambo, Y., Jalil, A. A., Triwahyono, S. & Abdulrasheed, A. A. Recent advances and future prospect in catalysts for oxidative coupling of methane to ethylene: A review. *Journal of Industrial and Engineering Chemistry* 59, 218-229 (2018).
7. Farrell, B. L., Igenegbai, V. O. & Linic, S. A Viewpoint on Direct Methane Conversion to Ethane and Ethylene Using Oxidative Coupling on Solid Catalysts. *ACS Catal.* 6, 4340-4346 (2016).
8. Keller, G. E. & Bhasin, M. M. Synthesis of ethylene via oxidative coupling of methane: I. Determination of active catalysts. *Journal of Catalysis* 73, 9-19 (1982).
9. Guo, X. et al. Direct, Nonoxidative Conversion of Methane to Ethylene, Aromatics, and Hydrogen. *Science* 344, 616-619 (2014).
10. Sakbodin, M., Wu, Y., Oh, S. C., Wachsman, E. D. & Liu, D. Hydrogen-Permeable Tubular Membrane Reactor: Promoting Conversion and Product Selectivity for Non-Oxidative Activation of Methane over an Fe©SiO2 Catalyst. *Angewandte Chemie* 128, 16383-16386 (2016).
11. Gerceker, D. et al. Methane Conversion to Ethylene and Aromatics on PtSn Catalysts. *ACS Catal.* 7, 2088-2100 (2017).
12. J. Spivey, J. & Hutchings, G. Catalytic aromatization of methane. *Chemical Society Reviews* 43, 792-803 (2014).
13. Xue, J. et al. Gas to Liquids: Natural Gas Conversion to Aromatic Fuels and Chemicals in a Hydrogen-Permeable Ceramic Hollow Fiber Membrane Reactor. *ACS Catal.* 6, 2448-2451 (2016).
14. Kiani, D., Sourav, S., Wachs, I. E. & Baltrusaitis, J. The Oxidative Coupling of Methane (OCM) by SiO2-Supported Tungsten Oxide Catalysts Promoted with Mn and Na. *ACS Catalysis* 49.
15. Wang, D. J., Rosynek, M. P. & Lunsford, J. H. Oxidative Coupling of Methane over Oxide-Supported Sodium-Manganese Catalysts. *Journal of Catalysis* 155, 390-402 (1995).
16. Arndt, S. et al. Mn—Na2WO4/SiO2 as catalyst for the oxidative coupling of methane. What is really known? *Applied Catalysis A: General* 425-426, 53-61 (2012).
17. Ito, T., Wang, J., Lin, C. H. & Lunsford, J. H. Oxidative dimerization of methane over a lithium-promoted magnesium oxide catalyst. *Journal of the American Chemical Society* 107, 5062-5068 (1985).
18. Schucker, R. C., Derrickson, K., Ali, A. & Caton, N. The effect of strontium content on the activity and selectivity of Sr-doped La2O3 catalysts in oxidative coupling of methane. *Applied Catalysis A: General* 117827 (2020) doi:10.1016/j.apcata.2020.117827.
19. Borchert, H. & Baerns, M. The Effect of Oxygen-Anion Conductivity of Metal-Oxide Doped Lanthanum Oxide Catalysts on Hydrocarbon Selectivity in the Oxidative Coupling of Methane. *Journal of Catalysis* 168, 315-320 (1997).
20. Zhao, M., Ke, S., Wu, H., Xia, W. & Wan, H. Flower-like Sr-La2O3 Microspheres with Hierarchically Porous Structures for Oxidative Coupling of Methane. *Ind. Eng. Chem. Res.* 58, 22847-22856 (2019).
21. Huang, P., Zhao, Y., Zhang, J., Zhu, Y. & Sun, Y. Exploiting shape effects of La2O3 nanocatalysts for oxidative coupling of methane reaction. *Nanoscale* 5, 10844-10848 (2013).
22. Hou, Y.-H., Han, W.-C., Xia, W.-S. & Wan, H.-L. Structure Sensitivity of La2O2CO3 Catalysts in the Oxidative Coupling of Methane. https://pubs.acs.org/doi/abs/10.1021/cs501733r (2015) doi:10.1021/cs501733r.
23. Kumar, G., Lau, S. L. J., Krcha, M. D. & Janik, M. J. Correlation of Methane Activation and Oxide Catalyst Reducibility and Its Implications for Oxidative Coupling. *ACS Catalysis* 6, 1812-1821 (2016).
24. Kuo, J. C. W., Kresge, C. T. & Palermo, R. E. Evaluation of direct methane conversion to higher hydrocarbons and oxygenates. *Catalysis Today* 4, 463-470 (1989).
25. Luo, L. et al. Gas-phase Reaction Network of Li/MgO-Catalyzed Oxidative Coupling of Methane and Oxidative Dehydrogenation of Ethane. *ACS Catalysis* (2019) doi: 10.1021/acscata1.8b04728.
26. Fleischer, V. et al. Investigation of the role of the Na2WO4/Mn/SiO2 catalyst composition in the oxidative coupling of methane by chemical looping experiments. *Journal of Catalysis* 360, 102-117 (2018).
27. Cheng, Z. et al. $C_2$ Selectivity Enhancement in Chemical Looping Oxidative Coupling of Methane over a Mg—Mn Composite Oxygen Carrier by Li-Doping-Induced Oxygen Vacancies. *ACS Energy Lett.* 3, 1730-1736 (2018).

28. Cruellas, A., Melchiori, T., Gallucci, F. & Annaland, M. van S. Advanced reactor concepts for oxidative coupling of methane. *Catalysis Reviews* 59, 234-294 (2017).

29. Tan, X. & Li, K. Oxidative Coupling of Methane in a Perovskite Hollow-Fiber Membrane Reactor. *Ind. Eng. Chem. Res.* 45, 142-149 (2006).

30. ten Elshof, J. E., Bouwmeester, H. J. M. & Verweij, H. Oxidative coupling of methane in a mixed-conducting perovskite membrane reactor. *Applied Catalysis A: General* 130, 195-212 (1995).

31. Czuprat, O., Schiestel, T., Voss, H. & Caro, J. Oxidative Coupling of Methane in a BCFZ Perovskite Hollow Fiber Membrane Reactor. *Ind. Eng. Chem. Res.* 49, 10230-10236 (2010).

32. Othman, N. H., Wu, Z. & Li, K. A micro-structured La0.6Sr0.4Co0.2Fe0.8O3-δ hollow fibre membrane reactor for oxidative coupling of methane. *Journal of Membrane Science* 468, 31-41 (2014).

33. Othman, N. H., Wu, Z. & Li, K. An oxygen permeable membrane microreactor with an in-situ deposited Bi1.5Y0.3Sm0.2O3-δ catalyst for oxidative coupling of methane. *Journal of Membrane Science* 488, 182-193 (2015).

34. Lu, Y. Oxygen-permeable dense membrane reactor for the oxidative coupling of methane. *Journal of Membrane Science* 170, 27-34 (2000).

35. Xu, S. J. & Thomson, W. J. Perovskite-type oxide membranes for the oxidative coupling of methane. *AIChE Journal* 43, 2731-2740 (1997).

36. Dimitrakopoulos, G., Koo, B., Yildiz, B. & Ghoniem, A. F. Highly Durable C2 Hydrocarbon Production via the Oxidative Coupling of Methane Using a BaFe0.9Zr0.1O3-δ Mixed Ionic and Electronic Conducting Membrane and La2O3 Catalyst. *ACS Catal.* 11, 3638-3661 (2021).

37. Arndt, S. et al. A Critical Assessment of Li/MgO-Based Catalysts for the Oxidative Coupling of Methane. *Catalysis Reviews* 53, 424-514 (2011).

38. Vamvakeros, A. et al. Real time chemical imaging of a working catalytic membrane reactor during oxidative coupling of methane. *Chemical Communications* 51, 12752-12755 (2015).

39. Igenegbai, V. O., Meyer, R. J. & Linic, S. In search of membrane-catalyst materials for oxidative coupling of methane: Performance and phase stability studies of gadolinium-doped barium cerate and the impact of Zr doping. *Applied Catalysis B: Environmental* 230, 29-35 (2018).

40. Igenegbai, V. O., Almallahi, R., Meyer, R. J. & Linic, S. Oxidative Coupling of Methane over Hybrid Membrane/Catalyst Active Centers: Chemical Requirements for Prolonged Lifetime. *ACS Energy Lett.* 1465-1470 (2019) doi:10.1021/acsenergylett.9b01075.

41. Bucher, E., Egger, A., Caraman, G. B. & Sitte, W. Stability of the SOFC Cathode Material Ba,Sr . . . Co,Fe . . . O3in CO2-Containing Atmospheres. *Journal of The Electrochemical Society* 8.

42. Ormerod, R. M. Solid oxide fuel cells. *Chem. Soc. Rev.* 32, 17-28 (2003).

43. Lin, Y. S. Inorganic Membranes for Process Intensification: Challenges and Perspective. *Ind. Eng. Chem. Res.* 58, 5787-5796 (2019).

44. Cruellas, A. et al. Oxidative Coupling of Methane in Membrane Reactors; A Techno-Economic Assessment. *Processes* 8, 274 (2020).

45. Wu, Z., Wang, B. & Li, K. A novel dual-layer ceramic hollow fibre membrane reactor for methane conversion. *Journal of Membrane Science* 352, 63-70 (2010).

46. de Jong, J., Benes, N. E., Koops, G. H. & Wessling, M. Towards single step production of multi-layer inorganic hollow fibers. *Journal of Membrane Science* 239, 265-269 (2004).

47. Balakotaiah, V., Sun, Z., Gu, T. & West, D. H. Scaling Relations for Autothermal Operation of Catalytic Reactors. *Ind. Eng. Chem. Res.* acs.iecr.0c05594 (2021) doi: 10.1021/acs.iecr.0c05594.

48. Sarkar, B., West, D. H. & Balakotaiah, V. Bifurcation analysis of oxidative coupling of methane in monolith, gauze or wire-mesh reactors. *Catalysis Today* (2021) doi:10.1016/j.cattod.2020.12.040.

49. Vandewalle, L. A., Van de Vijver, R., Van Geem, K. M. & Marin, G. B. The role of mass and heat transfer in the design of novel reactors for oxidative coupling of methane. *Chemical Engineering Science* 198, 268-289 (2019).

50. Ahmad, S. H. et al. Co-extruded dual-layer hollow fiber with different electrolyte structure for a high temperature micro-tubular solid oxide fuel cell. *International Journal of Hydrogen Energy* 42, 9116-9124 (2017).

51. Hufenus, R. et al. Melt-spun polymer fibers with liquid core exhibit enhanced mechanical damping. *Materials & Design* 110, 685-692 (2016).

52. Li, T. et al. X-ray tomography-assisted study of a phase inversion process in ceramic hollow fiber systems—Towards practical structural design. *Journal of Membrane Science* 528, 24-33 (2017).

53. Taniguchi, N., Hatoh, K., Niikura, J., Gamo, T. & Iwahara, H. Proton conductive properties of gadolinium-doped barium cerates at high temperatures. *Solid State Ionics* 53-56, 998-1003 (1992).

54. Ricote, S. & Bonanos, N. Enhanced sintering and conductivity study of cobalt or nickel doped solid solution of barium cerate and zirconate. *Solid State Ionics* 181, 694-700 (2010).

55. Stansch, Z., Mleczko, L. & Baerns, M. Comprehensive Kinetics of Oxidative Coupling of Methane over the La2O3/CaO Catalyst. *Ind. Eng. Chem. Res.* 36, 2568-2579 (1997).

56. Haag, S., van Veen, A. C. & Mirodatos, C. Influence of oxygen supply rates on performances of catalytic membrane reactors: Application to the oxidative coupling of methane. *Catalysis Today* 127, 157-164 (2007).

57. van Hassel, B. A., ten Elshof, J. E. & Bouwmeester, H. J. M. Oxygen permeation flux through La1-ySryFeO3 limited by carbon monoxide oxidation rate. *Applied Catalysis A: General* 119, 279-291 (1994).

58. Liang, W., Zhou, H., Caro, J. & Jiang, H. Methane conversion to syngas and hydrogen in a dual phase Ce0.8Sm0.2O2-δ-Sr2Fe1.5Mo0.505+δ membrane reactor with improved stability. *International Journal of Hydrogen Energy* 43, 14478-14485 (2018).

59. Li, W., Cao, Z., Li, H., Zhu, X. & Yang, W. Asymmetric dual-phase MIEC membrane reactor for energy-efficient coproduction of two kinds of synthesis gases. *International Journal of Hydrogen Energy* 44, 4218-4227 (2019).

60. Kim, J. H. et al. Nanoparticle Ex-solution for Supported Catalysts: Materials Design, Mechanism and Future Perspectives. *ACS Nano* 15, 81-110 (2021).

61. Zhu, C. et al. Electrochemical conversion of methane to ethylene in a solid oxide electrolyzer. *Nature Communications* 10, 1173 (2019).

62. Tan, X., Liu, Y. & Li, K. Preparation of LSCF Ceramic Hollow-Fiber Membranes for Oxygen Production by a Phase-Inversion/Sintering Technique. *Ind. Eng. Chem. Res.* 44, 61-66 (2005).

63. Hufenus, R. et al. Melt-spun polymer fibers with liquid core exhibit enhanced mechanical damping. *Materials & Design* 110, 685-692 (2016).

64. Li, T. et al. X-ray tomography-assisted study of a phase inversion process in ceramic hollow fiber systems—Towards practical structural design. *Journal of Membrane Science* 528, 24-33 (2017).

65. Accardo, G., Spiridigliozzi, L., Yoon, S. P. & Dell'Agli, G. Li/Gd co-doped Barium-cerate perovskites as proton-conducting electrolytes for LT-SOFCs. in 020032 (2019). doi:10.1063/1.5140305.

66. Li, S. et al. Feasibility and mechanism of lithium oxide as sintering aid for Ce0.8Sm0.2Oδ electrolyte. *Journal of Power Sources* 205, 57-62 (2012).

What is claimed is:

1. An asymmetric hollow fiber membrane for oxidative coupling of methane, comprising:

an inner bore having an inner diameter;

an inner porous layer surrounding the inner bore, the inner porous layer having an interconnected network of pores defined therein; and an outer separation layer surrounding the inner porous layer, the outer separation layer being substantially non-porous, wherein the inner porous layer comprises an oxidative coupling of methane (OCM) catalyst and the outer separation layer comprises a membrane for oxygen separation and transport through the outer separation layer, the inner porous layer has a thickness as measured from an outer circumferential edge of the inner bore to an interface between the inner porous layer and the outer separation layer, the outer separation layer has a thickness as measured from the interface to an outer circumferential edge of the hollow fiber membrane, the thickness of the inner porous layer is greater than the thickness of the outer separation layer, the outer separation layer has a thickness of about 5 μm to 100 μm, and the thickness of the inner porous layer, the thickness of the outer separation layer, and a porosity of the inner porous layer are each selected such that a rate of transport of oxygen through the outer separation layer equals a rate of methane activation at the inner porous layer when a methane containing source is flowed through the inner porous layer and an oxygen source is flowed through the outer separation layer at a temperature of about 700° C. to 900° C.

2. The membrane of claim 1, wherein the inner porous layer comprises one or more of barium cerate doped with gadolinium (BCG), $Mn/Na_2WO_4/SiO_2$, $Bi_{1.5}Y_{0.3}Sm_{0.2}O_{3-x}$ (BYS), $SrO/La_2O_3$, and Li/MgO and/or wherein, the outer separation layer comprises one or more of BCG, $La_{0.6}Sr_{0.4}CO_{0.2}Fe_{0.8}O_{3-x}$ (LSCF), $BaCo_xFe_yZr_z$ (BCFZ, x+y+z=1), $BaFe_{0.9}Zr_{0.1}O_{3-x}$, $Ba_{0.5}Sr_{0.5}CO_{0.8}Fe_{0.2}O_{3-x}$ (BSCF), and $CeO_{0.8}$—$Gd_{0.2}O_{2-x}$ (BSCF-GDC).

3. The membrane of claim 1, further comprising an inert layer arranged between the inner porous layer and the outer separation layer.

4. The membrane of claim 1, wherein both the inner porous layer and the outer separation layer are formed of barium cerate doped gadolinium (BCG).

5. The membrane of claim 1, wherein the outer diameter of the membrane is about 0.5 mm to about 3 mm and the inner diameter of the membrane is about 0.3 mm to about 2.5 mm.

6. The membrane of claim 1, wherein the thickness of the inner porous layer is about 250 μm to about 1300 μm.

7. The membrane of claim 1, wherein the interface is free of visible cracks and/or defects.

8. The membrane of claim 1, wherein the inner porous layer has a porosity of up to about 30%.

9. A method of converting methane to a target product comprising ethylene and/or other $C_2$+ hydrocarbons through oxidative coupling of methane, comprising exposing the membrane of claim 1 to a methane containing source in the presence of oxygen, wherein the inner porous layer catalyzes an oxidative coupling of methane reaction and the outer separation layer is a membrane for the transport of oxygen to the inner porous layer.

10. A method of converting methane to a target product comprising ethylene and/or other $C_2$+ hydrocarbons through oxidative coupling of methane, comprising exposing the membrane of claim 1 to a methane containing source in the presence of oxygen, wherein the inner porous layer catalyzes an oxidative coupling of methane reaction, and the outer separation layer is a membrane for the transport of oxygen to the inner porous layer.

11. The method of claim 9, wherein the oxygen is fed as $O^2-$ through the membrane or is fed as $O_2(g)$ with the methane containing source.

12. The method of claim 10, wherein the oxygen is fed as $O^{2-}$ through the membrane or is fed as $O_2(g)$ with the methane containing source.

13. The method of claim 9, wherein the method is performed at a temperature of about 700° C. to about 900° C.

14. The method of claim 9, wherein the $C_{2+}$ selectivity is at least about 65% for a $CH_4$ conversion of at least 30% and/or wherein greater than about 0.2 mL of target product is formed per minute per $cm^2$ of membrane.

15. The method of claim 10, wherein the $C_{2+}$ selectivity is at least about 65% for a $CH_4$ conversion of at least 30% and/or wherein greater than about 0.2 mL of target product is formed per minute per $cm^2$ of membrane.

16. A method of making an asymmetric hollow fiber membrane according to claim 1, comprising co-extruding a porous layer precursor suspension, a separation layer precursor suspension and an internal coagulant to form a precursor fiber, wherein the suspensions undergo a phase inversion process;

solidifying the precursor fiber; and sintering the precursor fiber to form the asymmetric hollow fiber, wherein:

the porous layer precursor suspension comprises a BCG precursor, a solvent, a polymer, a pore forming additive, and a phase inversion additive, the separation layer precursor suspension comprises the BCG precursor, a solvent, a polymer, and a phase inversion additive, the BCG precursor comprises stoichiometric amounts of $BaCO_3$, $CeO_2$, and $Gd_2O_3$ such that upon sintering a barium cerate doped with gadolinium is formed, and the hollow fiber comprises an inner porous layer comprising the barium cerate doped with gadolinium and an interconnected network of pores surrounding an inner bore, and an outer separation layer comprising the barium cerate doped with gadolinium surrounding the inner porous layer.

17. The method of claim 16, wherein the precursor fiber is solidified in an aqueous solution comprising a sintering aid or wherein the precursor fiber is sintered in a sacrificial bath comprising the BCG precursor.

18. The method of claim 16, wherein the pore forming additive is present in an amount about 5 wt % to about 30 wt % based on the total weight of the porous layer precursor suspension and/or wherein the pore forming additive is graphite.

19. The method of claim 16, wherein the solvent is present in the porous layer precursor suspension and/or the separation layer precursor suspension about 20 wt % to about 40 wt % based on the total weight of the respective one of the porous layer precursor suspension or the separation layer precursor suspension and/or wherein the solvent in the porous layer precursor suspension and/or the separation layer precursor suspension is one or more of dimethylsulfoxide (DMSO), n-methyl pyrrolidone (NMP), and dimethylformamide (DMF).

20. The method of claim 16, wherein the polymer is present in the inner porous layer precursor suspension and/or the separation layer precursor suspension about 4 wt % to about 10 wt % based on the total weight of the respective one of the inner porous layer precursor suspension or the separation layer precursor suspension and/or wherein the polymer in the porous layer precursor suspension and/or the separation layer precursor suspension is polyethersulfone (PES) and/or cellulose acetate.

21. The method of claim 16, wherein the phase inversion additive is present in the porous layer precursor suspension and/or the separation layer precursor suspension about 0.1 wt % to about 3 wt % based on the total weight of the respective one of the porous layer precursor suspension or the separation layer precursor suspension and/or the phase inversion additive in the porous layer precursor suspension and/or the separation layer precursor suspension is polyvinylpyrrolidone (PVP).

22. The method of claim 16, wherein the internal coagulant comprises one or more of water and polyvinyl alcohol.

23. The method of claim 22, wherein the internal coagulant comprises both water and polyvinyl alcohol, and the water is present in an amount of about 70 wt % to about 100 wt % based on the total weight of the internal coagulant and the PVA is present in an amount of about 0 wt % to about 30 wt % based on the total weight of the internal coagulant.

24. The method of claim 16, wherein the coextrusion is performed through a triple orifice spinneret.

25. The fiber of claim 1, wherein the inner porous layer is formed of a different material than the outer separation layer.

* * * * *